US012161536B2

(12) United States Patent
Semidey-Flecha et al.

(10) Patent No.: US 12,161,536 B2
(45) Date of Patent: Dec. 10, 2024

(54) TAMPON WITH WICKING MEMBER ADAPTED FOR IMPROVED MANUFACTURABILITY AND WICKING PERFORMANCE

(71) Applicant: The Procter & Gamble Company, Cincinnati, OH (US)

(72) Inventors: Lymarie Semidey-Flecha, West Chester, OH (US); Kristzian M. Balajti, Csomor (HU); Peter Gazsi, Csomor (HU); Ryo Minoguchi, Cincinnati, OH (US); Laszlo Pozsgai, Csomor (HU); Khalid Qureshi, Mason, OH (US); Kevin C. Strong, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 325 days.

(21) Appl. No.: 17/723,522

(22) Filed: Apr. 19, 2022

(65) Prior Publication Data

US 2022/0331171 A1 Oct. 20, 2022

Related U.S. Application Data

(60) Provisional application No. 63/176,926, filed on Apr. 20, 2021.

(51) Int. Cl.
*A61F 13/20* (2006.01)
*A61F 13/34* (2006.01)
(Continued)

(52) U.S. Cl.
CPC ...... *A61F 13/2071* (2013.01); *A61F 13/2051* (2013.01); *A61F 13/34* (2013.01);
(Continued)

(58) Field of Classification Search
CPC .............. A61F 13/2051; A61F 13/2068; A61F 13/34; A61F 13/2071; A61F 13/53708; A61F 13/53752
See application file for complete search history.

(56) References Cited

U.S. PATENT DOCUMENTS

| 2006/0025742 A1 | 2/2006 | Hasse et al. |
| 2006/0025743 A1 | 2/2006 | Hasse et al. |

(Continued)

FOREIGN PATENT DOCUMENTS

| GB | 2227666 A | 8/1990 |

OTHER PUBLICATIONS

PCT Search Report and Written Opinion for PCT/US2022/025263 dated Jul. 8, 2022, 12 pages.

*Primary Examiner* — Susan S Su
(74) *Attorney, Agent, or Firm* — Sarah M. DeCristofaro; William E. Gallagher

(57) ABSTRACT

The disclosed tampon may include a pledget having a rearward end; a wicking member having a trailing portion trailing the rearward end and having a rearward edge; and a withdrawal cord with an attached portion attached to the pledget and a free portion trailing the rearward edge. In an opened condition the pledget has a pair of side edges and a pledget width, and includes fibrous absorbent material and an outer cover of a first section of nonwoven web at least partially covering the absorbent material, the trailing portion of the wicking member including at least four layers of nonwoven web, at least one of which is an extension of the first section of nonwoven web. The wicking member may have a width substantially equal to the pledget width; and the trailing portion may have a length of at least about 10 mm and no greater than about 60 mm.

19 Claims, 12 Drawing Sheets

(51) Int. Cl.
 *A61F 13/537* (2006.01)
 *A61F 13/53* (2006.01)
(52) U.S. Cl.
 CPC ................. *A61F 13/53708* (2013.01); *A61F 13/53752* (2013.01); *A61F 2013/530036* (2013.01); *A61F 2013/530233* (2013.01); *A61F 2013/530386* (2013.01)

(56) References Cited

U.S. PATENT DOCUMENTS

2008/0177241 A1  7/2008 Hasse et al.
2014/0115844 A1* 5/2014 Wolter ................ A61F 13/2077
 28/118

* cited by examiner

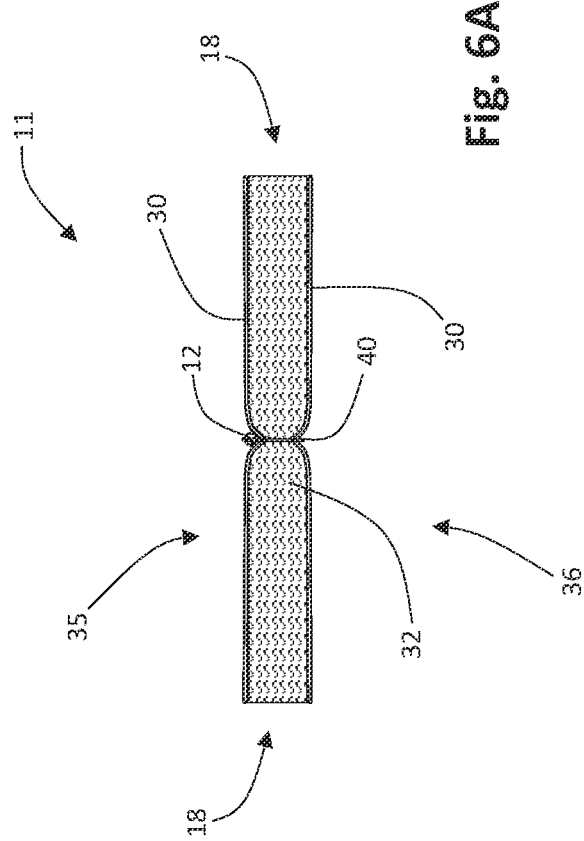

TAMPON WITH WICKING MEMBER ADAPTED FOR IMPROVED MANUFACTURABILITY AND WICKING PERFORMANCE

CROSS REFERENCE TO RELATED APPLICATION

This application claims the benefit of U.S. Provisional Application No. 63/176,926, filed Apr. 20, 2021, the substance of which is incorporated herein by reference.

BACKGROUND OF THE INVENTION

A variety of designs for absorbent tampons have been manufactured for a number of years, and used by women to capture and absorb menstrual fluid internally, in conjunction with, or as an alternative to, externally worn feminine hygiene pads. Many women prefer to use tampons as an alternative to feminine hygiene pads at least some of the time during menstruation. Among other reasons for such preference, because tampon use is internal it is more discrete, avoiding the bulk under clothing that is associated with many types of feminine hygiene pads.

Particularly when a feminine hygiene pad is not used in conjunction therewith, it is important that the tampon capture and absorb most if not substantially all of the menstrual fluid that is discharged during the tampon's usage duration (to the extent of its absorption capacity), to help avoid a leakage of fluid that may soil underwear, outer clothing, bedclothes, etc. The prior art has recognized various ways in which tampons might fail to perform effectively. One such way is sometimes referred to as "bypass" failure. Bypass failure occurs when the menstrual fluid travels along the walls of the vaginal cavity without contacting the tampon, or the tampon, while having available absorption capacity, otherwise fails to capture and absorb the fluid.

A variety of approaches to tampon design have sought to mitigate such failure. One approach that has proven effective has been to include a wicking member as part of the withdrawal cord. The wicking member is a material/structure selected and configured to extend downward (or trail, to the rear of) the main pledget, along with the withdrawal cord, thereby extending further down the vaginal cavity toward the vaginal opening than the pledget, following insertion. Appropriately configured, the wicking member can engage menstrual fluid flowing along the vaginal cavity past the pledget, capture it, and wick it back to the pledget. Current approaches to manufacture of such tampons, however, have shown to be inefficient, and current selections of configurations and materials have shown to be less effective than might be hoped.

Accordingly, there remains room for improvement in the construction and method of manufacture of tampons with wicking members.

BRIEF DESCRIPTION OF THE DRAWINGS

FIG. 6A is a schematic lateral cross section of components of the tampon shown in FIG. 2, taken through line 6-6 in FIG. 2, shown with the components held together by stitches.

DETAILED DESCRIPTION OF EXAMPLES

Definitions

Figure 1:
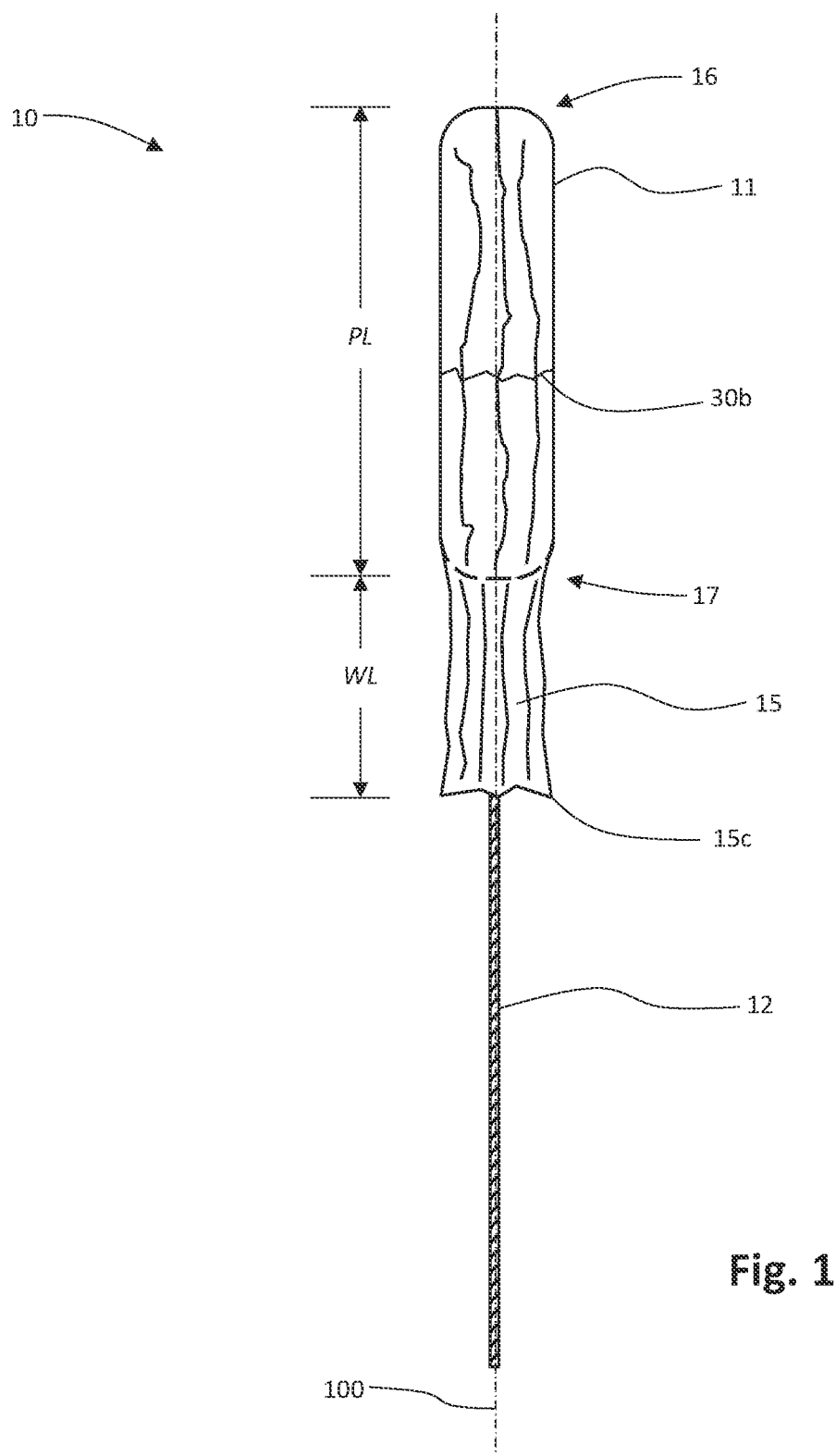
FIG. 1 is a longitudinal side view of an example of a tampon with a pledget shaped and compressed into a self-sustaining form, with a wicking member.

As used herein the term "tampon" refers to any type of absorbent structure which is inserted into the vaginal cavity for the absorption of fluid therefrom. Typically, a tampon includes a pledget structure including a quantity of absorbent material, often absorbent fibrous material, which pledget structure has been bunched, folded and/or compressed in one or more lateral/radial directions, the longitudinal direction, or both, via application of pressure, heat and/or moisture control, in order to provide a formed tampon having a size, shape (typically cylindrical) and stability of form to facilitate insertion into the vagina. A tampon which has been so formed is referred to herein has a "self-sustaining" form. The degree of compression, heat and moisture control applied to the pledget is sufficient such that in the subsequent absence of the external forces and absence of substantial contact with moisture, the pledget will tend to retain its general formed shape and size. It will be understood by persons of ordinary skill in the art that this self-sustaining form typically does not persist following insertion of the tampon. Once the tampon is inserted and begins to contact and absorb fluid, the pledget will swell with absorbed fluid and lose its self-sustaining form.

As used herein the terms "pledget" or "tampon pledget" are intended to be interchangeable and refer to a structure including absorbent material configured to perform the primary function of the tampon, absorption of menstrual fluid. A tampon pledget is sometimes referred to as a tampon blank, or a softwind, and the term "pledget" is intended to include structures designated by such terms as well.

As used herein "vaginal cavity" refers to the internal space within the genitalia of the human female, located between the introitus of the vagina (sometimes referred to as the sphincter of the vagina) and the cervix.

With respect to a tampon, the "longitudinal" direction is the ordinary general direction of ejection from an applicator; and also corresponds with the ordinary general direction of insertion of a tampon into and its withdrawal from the vaginal cavity in normal use. For a completely manufactured, pre-use tampon that has a pledget with a generally cylindrical or capsule-shaped self-sustaining form, the longitudinal axis of the form lies generally or approximately along the longitudinal direction. A "radial" or "lateral" direction is a direction perpendicular to the longitudinal direction. The "lateral" direction is perpendicular to the longitudinal direction, and perpendicular to the z direction (defined below). Unless otherwise specified, references to "length" herein refer to a dimension along the longitudinal direction; references to "width" herein refer to a dimension along the lateral direction.

A "nonwoven," "nonwoven web," "nonwoven web material," or "nonwoven fabric" is a cloth-like web material (or portion or section thereof) formed predominantly of fibers that are neither knitted nor woven, but rather, laid down and accumulated to a desired basis weight, then consolidated and held together to form a web, via one or any combination of calendering, thermal and/or compression bonding, bonding via use of a binder, heating (via, e.g., heated air driven through an accumulation of fibers) or hydroentangling (spunlace). The predominant fibers may be natural fibers harvested from plant material (e.g., cotton) (but excluding tree wood pulp), semi-synthetic (e.g., rayon, lyocell, viscose), or synthetic (e.g. fibers spun from molten thermoplastic polymer resin(s)), or any combination thereof. Herein, a skin- or membrane-like film (e.g., extruded or otherwise formed from polymer resin(s)) is not deemed a nonwoven. Herein, a paper tissue product, paper product, or paperboard or cardboard product, formed via wetlaying and predominantly constituted of tree wood pulp, is not deemed a nonwoven.

"Opened configuration," with respect to a tampon, means the configuration of the tampon prior to the time it is compressed and formed into a self-sustaining form during manufacture, or in the case of a finished product, after it is completely ejected from an applicator (if present) and/or allowed and/or caused by any suitable technique to open and substantially re-assume its pre-compression shape and size.

"Predominant," and forms thereof, when used to characterize a quantity of a component present in a material, means that a majority of the weight of the material is constituted by the component.

"Withdrawal cord" refers to any section of string, yarn, cord, ribbon, strip material or other flexible/pliable elongate structure typically (although not necessarily) formed of fibrous material, attached to and/or extending from a tampon pledget and trailing from its rearward end. A withdrawal cord of sufficient length may be provided with a tampon for the purpose of providing a relatively thin and flexible trailing member of sufficient length to allow for a portion thereof to trail and remain outside of the introitus following full insertion of the tampon, which the user may easily grasp and pull to withdraw the tampon from her body following a desired duration of use.

With respect to a nonwoven web material or an uncompressed pledget as described herein, laid out flat on a horizontal planar surface, the "z direction" is a direction orthogonal to the horizontal planar surface, and is the direction along which caliper or thickness of a nonwoven web material or pledget would be measured.

The present disclosure relates to an improved absorbent tampon provided with a leakage protection feature. It has been found that there are several potential mechanisms beyond simple bypass flow which may contribute to tampon leakage. Without wishing to be bound by theory, some of these mechanisms may be explained by the following observations. It has been found that many current tampons show stains along the length of the withdrawal cord following use and withdrawal, associated with incidents of tampon leakage. It is believed that the withdrawal cord of many current tampons may offer an escape route for menstrual fluid present at the base of the vaginal cavity, by operating as a wicking mechanism.

During a tampon change, some residual menstrual fluid may be left in the vaginal cavity near the introitus. This may be fluid that was absorbed by the tampon prior to removal, but is subsequently expressed from the tampon as it is drawn out of the body through the relatively narrow sphincter of the vagina. Such residual fluid, particularly if located near the introitus (i.e. in the lower vaginal cavity) may not be effectively absorbed by the replacement tampon. This is particularly true of many current tampons which are typically inserted somewhat more deeply into the vaginal cavity. These circumstances, as well as bypass leakage described above, and other leakage circumstances are addressed by tampons within contemplation of the present disclosure.

Pledget and Withdrawal Cord

FIGS. 1, 2, 3A, 4, 5 and 6A and 3B show one non-limiting example of such an absorbent tampon 10, having a longitudinal axis 100, a pledget 11 having a forward end 16 and a rearward end 17 and a withdrawal cord 12 attached to the pledget and having an attached portion 12a attached to the pledget and a free portion 12b extending rearward from a location proximate the rearward end 17. Generally, the "pledget" as referred to herein is that portion of the tampon that includes the main body and mass of absorbent material 32, but does not include withdrawal cord 12. Tampons contemplated herein, however, are not limited to structures having the particular configuration shown in the drawings.

Figure 2:
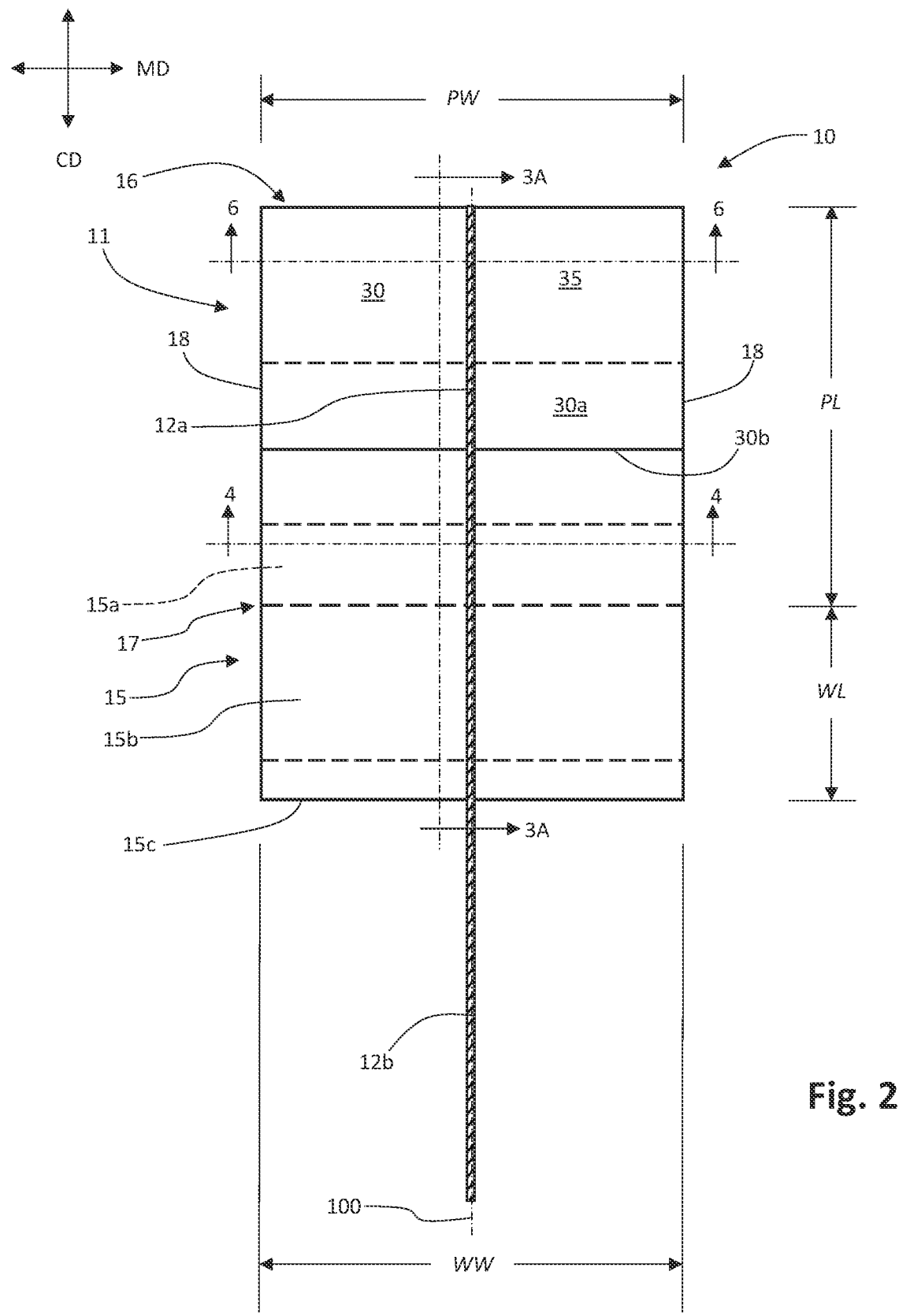
FIG. 2 is a longitudinal front side view of an example of a tampon before the pledget has been shaped and compressed into a self-sustaining form.
Figure 3A:
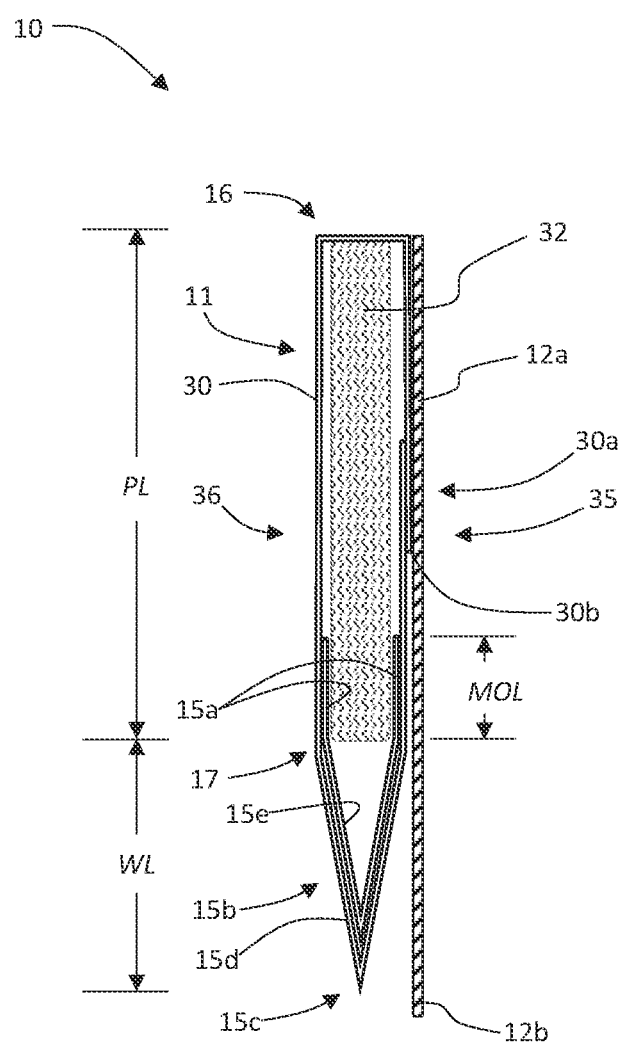
FIG. 3A is a schematic longitudinal cross section of components of the tampon shown in FIG. 2, taken through line 3A-3A in FIG. 2, shown with the components slightly separated for visibility.
Figure 6B:
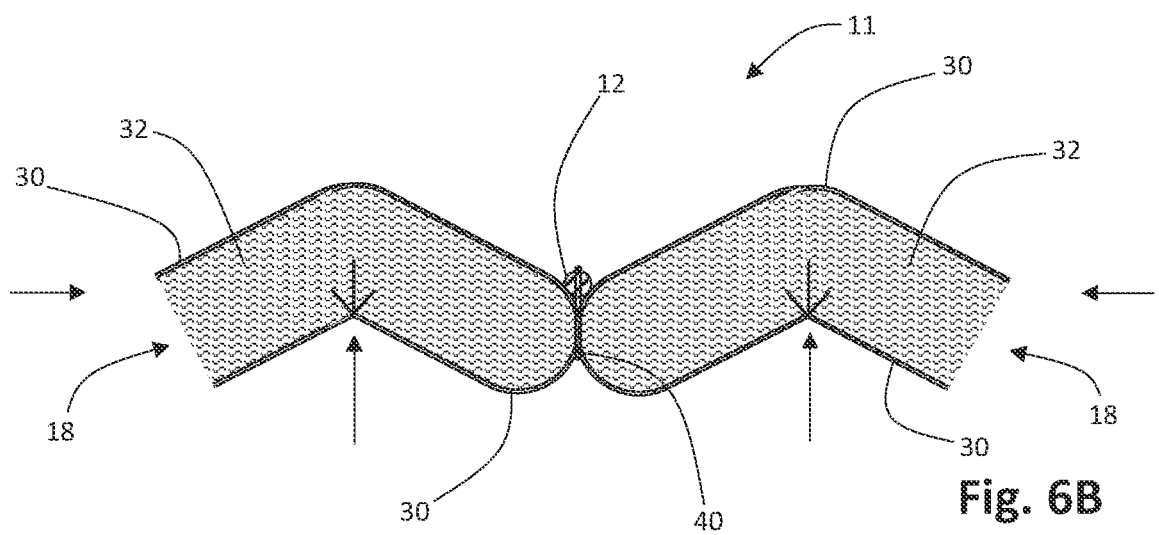
FIGS. 6B-6D are schematic lateral cross sections of components of the tampon as shown in FIG. 6A, in successive stages of predominantly lateral compression into a self-sustaining form.
Figure 6C:
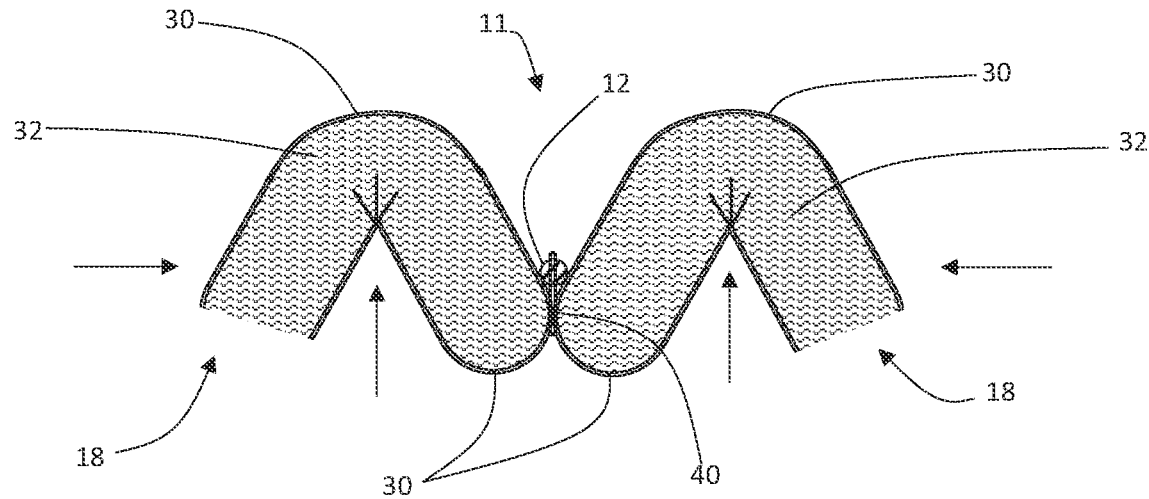
Figure 6D:
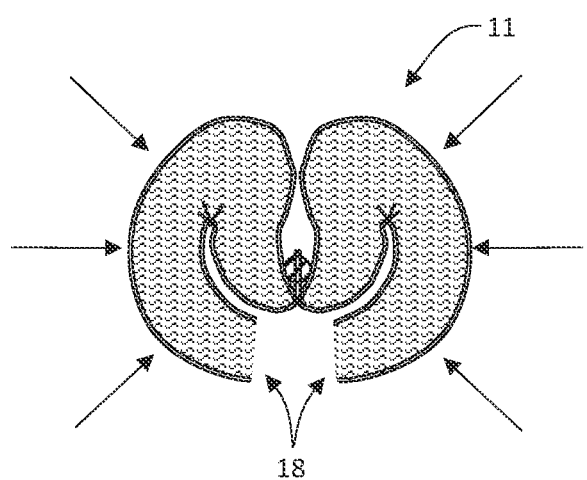

The pledget 11 of the tampon 10 as shown in FIGS. 1 and 2 has a forward end 16 and a rearward end 17. During manufacture of the tampons the pledget 11 may be folded, bunched, compressed and/or otherwise formed in size and shape, from its initially manufactured configuration (e.g. as shown in FIGS. 2 and 3A) into a generally cylindrical and/or capsule-shaped configuration (e.g. as shown in FIG. 1) along a radial direction, the lateral direction, longitudinal direction, or in some combination thereof. While the pledget 11 may be formed into a substantially cylindrical and/or capsule-shaped configuration a suggested in FIG. 1, other shapes are also possible. These may include shapes having a lateral cross section which may be described as oval, elliptical, ovoid, stadium, rectangular, triangular, trapezoidal, semi-circular, or other suitable shapes. In the example depicted in FIGS. 1, 2 and 6A-6D, the pledget 11 may be compressed to its greatest extent, or primarily, in the lateral direction, to the shape of its self-sustaining form. (For purposes herein, a "primary" direction of compression is the direction along which greatest displacement of the pledget body occurs, in the transition from its uncompressed form to its compressed, self-sustaining form.) The means of lateral compression may induce the pledget to fold up in the z-direction as suggested in FIGS. 6B-6D, as the side edges 18 are urged laterally toward the longitudinal axis. The pledget may be compressed laterally to a self-sustaining form by use of equipment and processes described in, for example, US2005/0027275 and/or US2008/0262464.

Figure 3B:
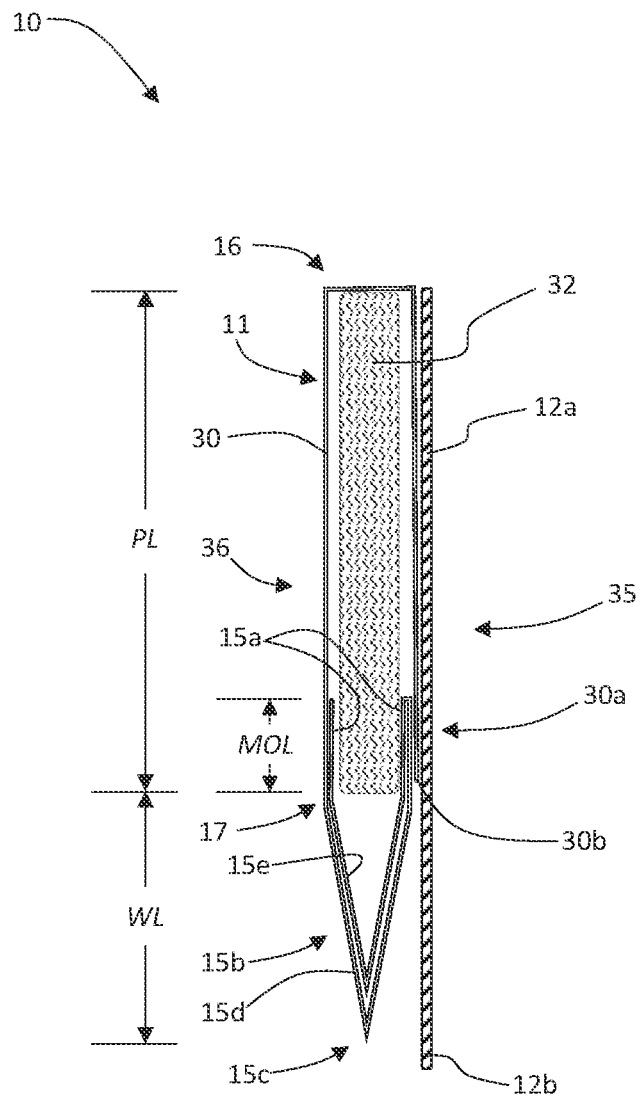
FIGS. 3B and 3C are schematic longitudinal cross sections of alternative embodiments to that shown in FIG. 3A.
Figure 3C:
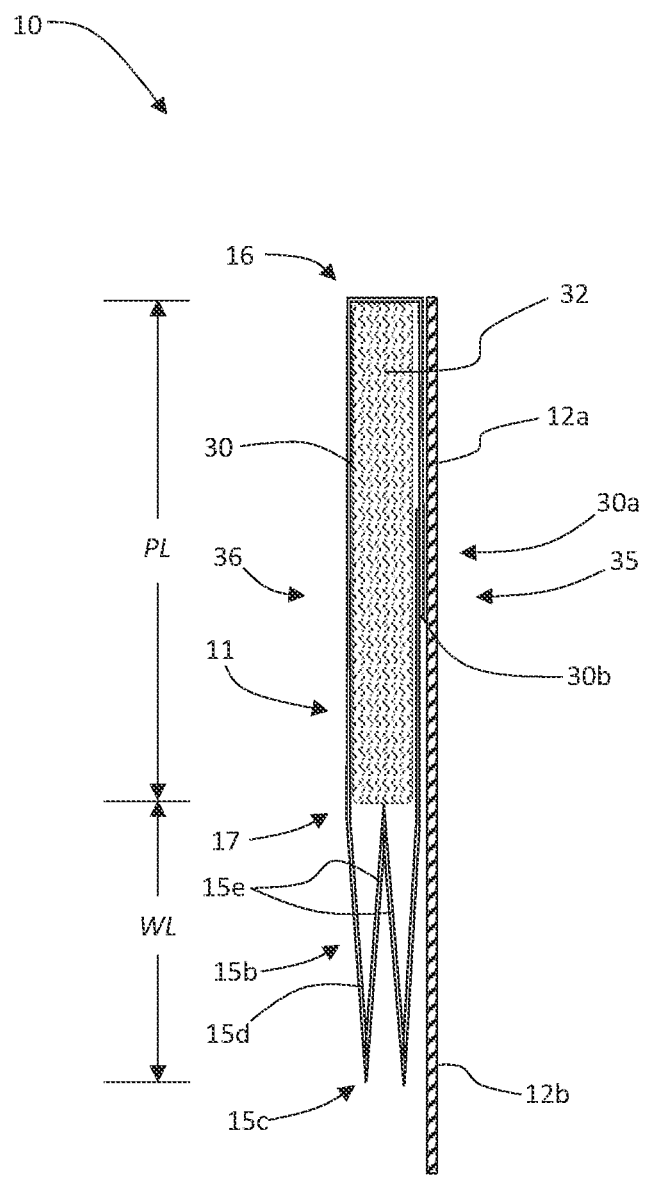
Figure 4:
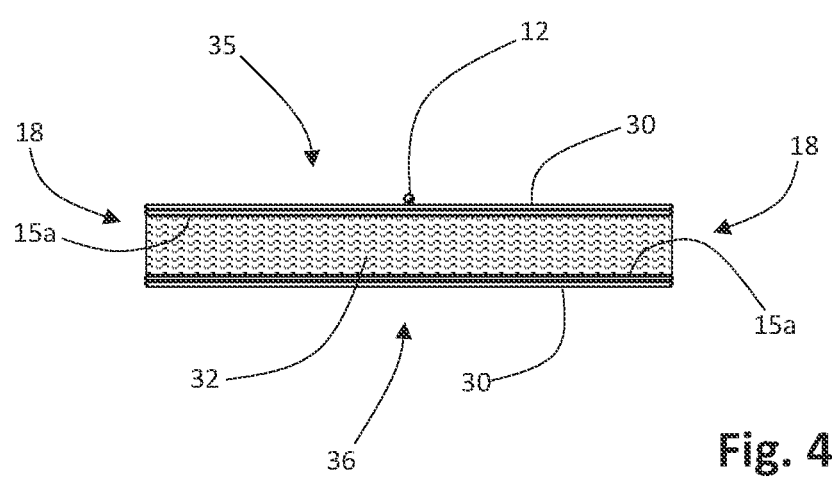
FIG. 4 is a schematic lateral cross section of components of the tampon shown in FIG. 2, taken through line 4-4 in FIG. 2, shown with the components slightly separated for visibility.

The pledget contemplated herein may have any other suitable form and structure, for example, as depicted in FIGS. 3B-3C. Other non-limiting examples of suitable pledget forms, material composition and structure are depicted and described in US2010/0268182 and US2007/0260211.

A wicking member 15, described in greater detail below, may be joined to either a withdrawal cord 12, the pledget 11 itself, or both. This joining of the wicking member may occur prior or subsequent to compression of the pledget 11 to a self-sustaining form. In some variations it may be desirable to attach some or all of the wicking member 15 to the pledget 11, the withdrawal cord 12, or both, prior to compression of the pledget 11 to a self-sustaining form. In one method of making of a tampon 10, described more fully below, the wicking member 15 may be integral with the pledget 11 prior to compression of the pledget. In any of the above mentioned manners of construction, the trailing portion 15b of wicking member 15 is preferably not compressed with the pledget 11; or, if compressed, is not compressed to the same degree as the pledget 11.

Prior to formation into a self-sustaining form, the pledget 11 may be of any suitable shape, size, material, or configuration. In the non-limiting example shown in FIGS. 2, 3A and 4, pledget 11 includes a batt or other mass of absorbent material 32, disposed within an outer cover 30. This type pledget may be formed on a continuous processing line wherein absorbent fibrous material is continuously deposited (e.g., via an airlaying process) to form a continuous batt having a desired cross-direction width and depth/weight, onto a continuous web of cover material being conveyed along a machine direction. The cover material web may then be wrapped about the batt by suitable web guiding and folding equipment, to form a continuous wrapped batt. Individual pledgets may then be cut from the continuous batt by repetitive die cutting across the moving batt (i.e., cutting along the cross direction). In the non-limiting examples depicted herein, the cross direction CD is parallel with the longitudinal direction relative the pledget, as indicated in FIG. 2. The cross-direction cuts may be linear, which will result in rectangular pledgets. Alternatively, in some examples (not specifically depicted), the cross-direction cuts may be non-linear; the cutting tool may be configured to make cuts forming the respective side edges 18 of each successive pledget, to impart the side edges with respective arched or curved profiles. In such examples, a curved side edge profile may help facilitate subsequent compression and formation into a cylindrical or capsule-shaped form with rounded or otherwise tapered forward and rearward ends, through a graduating reduction or tapering down, via the cut profile, in the bulk/quantity of material that must be compressed at forward and rearward ends 16, 17. Various shapes that embody a tapering down of the quantity of material present toward the forward and rearward ends of the pledget are contemplated.

While the pledgets 11 shown in FIGS. 2 and 3A-3C are depicted as approximately rectangular in shape along broad surfaces 35, 36, other shapes may be used for tampons within contemplation of the present disclosure. It may be desired, however, that the cut profile be configured to form respective cut edges of respectively leading and trailing pledgets being cut from the batt as it moves through the manufacturing line, with no generation of cutoff waste/scrap. It can be appreciated that the non-limiting example of a straight edge cut profile reflected in FIG. 2 provides this benefit.

In other examples (not specifically shown), the pledget 11 and/or absorbent material 32 may be a laminar structure including integral or discrete layers. As noted, in the examples shown in FIGS. 2 and 3A-3C, the pledget 11 may include an enveloping cover 30 and one or more layers of absorbent material 32 positioned within the cover. In other examples, the pledget need not have a layered structure at all. To facilitate compression into its self-sustaining form the pledget 11 may be folded, e.g., as depicted herein, may be rolled (e.g. as in currently marketed U BY KOTEX brand tampons, a product of Kimberly-Clark Worldwide, Inc., Irving, TX), may comprise a "petal" structure (e.g. of overlaying/underlaying, crossing rectangular patches of absorbent material, in a configuration present in PLAYTEX SPORT brand tampons, a product of Edgewell Personal Care LLC, Chesterfield, MO) or any other of the structures and configurations which are known in the art relating to tampon pledgets and their manufacture.

The pledget 11 and absorbent material 32 therein may include a wide variety of liquid-absorbing materials commonly used for absorbency in absorbent articles, such as but not limited to rayon fiber, cotton fiber, wood pulp fiber and comminuted wood pulp fiber (sometimes called "airfelt"). Examples of other suitable absorbent materials may include creped cellulose wadding; spun and/or meltblown polymer fibers or filaments; chemically stiffened, modified or cross-linked cellulosic fibers; other synthetic fibers such as polyamide fibers (e.g., nylon fibers); peat moss; absorbent foams (such as open-celled foam formed through polymerization of a high internal phase water-in-oil emulsion); nonwoven web materials of natural and/or synthetic fibers or combinations thereof, tissue including tissue wraps and tissue laminates; or any equivalent material or combinations of materials, or blends or combinations of these. Suitable fibers include rayon. (Herein, the term "rayon" is used generically to refer to fibers spun from regenerated cellulose, and includes, but is not necessarily limited to, viscose, MODAL, TENCEL (or lyocell); tri-lobal and conventional rayon fibers, and needle punched rayon). Suitable cotton fibers may include long fiber cotton, short fiber cotton, cotton linters, T-fiber cotton, card strips, and comber cotton. Preferably, the cotton fibers or fabric layer thereof should be scoured (for removal of natural hydrophobic waxes and impurities) and bleached (for whiteness) and may be imparted with a glycerin finish (for enhancing compaction), a leomin finish (for lubricity), or other suitable finish. Additionally, superabsorbent materials, such as superabsorbent polymers or absorbent gelling materials may be incorporated into the pledget. In particular examples it may be desired that rayon or cotton or a blend thereof, constitute the greater proportion (by weight) of the absorbent material 32; that cotton alone constitute the greater proportion (by weight) or substantially all of the absorbent material 32, or that rayon alone constitute the greater proportion (by weight) or substantially all of the absorbent material 32, since rayon fibers may possess absorbency properties or capacity greater than those of other fibrous materials, per unit weight and/or per unit cost.

In the examples shown in FIGS. 2 and 3A-3C, the pledget 11 may be formed of a body or batt of soft absorbent fibrous material 32 such as rayon fibers or cotton fibers or a combination or blend thereof, and the cover 30 may be formed of a woven, knitted or nonwoven web fabric material of suitable composition. The materials for the body of absorbent material 32 may have the form of nonwoven or woven fabric or a batt formed by any suitable process such as airlaying, carding, wetlaying, hydroentangling, or other known fiber deposition and consolidation techniques.

The absorbent material 32 of the pledget 11 may be surrounded or wrapped by a liquid permeable cover 30. Cover materials may include rayon, cotton, spunbond monocomponent, bicomponent or multicomponent fibers spun from polymer resins, or other suitable natural or synthetic fibers known in the art. If the pledget 11 is layered, the layers may include different materials. For instance, in the example shown in FIG. 3A the cover 30, may be constituted primarily of rayon, while the absorbent material 32 may be constituted primarily of cotton. In other examples the cover may be constituted primarily of cotton, and the intermediate layer or layers may be constituted primarily of rayon. Optionally, the entire pledget 11 may be formed of a uniform or nonuniform blend of materials throughout. In another particular example, cover 30 may be formed of a nonwoven web of spunbond fibers. The spunbond fibers may be spun from, for example, polymer resin including polyolefins such as polypropylene, polyethylene, or a blend or combination thereof. In a more particular embodiment the spunbond fibers may be spun bicomponent fibers including a first polypropylene resin component and a second differing polypropylene resin component or a polyethylene resin component. When formed of ordinarily hydrophobic materials such as polyolefins (including polypropylene and polyethylene) cover 30 material may be treated, e.g., by application of a suitable surfactant, to render it hydrophilic, so that it will readily attract and permit aqueous fluid to wick therethrough to the absorbent material within the cover. A nonwoven web material formed of polymeric material as described may be desired to form the cover, over natural fibrous materials or semi-synthetic rayon, for reasons of having a soft, smooth and comfortable feel and low friction against sensitive skin and internal tissues, relatively low cost and suitable wet structural/mechanical integrity. In some circumstances, however, it may be desired that the nonwoven web material forming outer cover 30 be composed of a blend of fibers selected for having differing properties, to be combined in a material having a complementary or synergistic combination of properties when these materials form an outer cover covering the absorbent material 32 of the pledget. Generally, it may be desired that the absorbent material 32 of the pledget have a greater attraction for (aqueous) menstrual fluid, than the nonwoven material forming the outer cover 30. While it will be desired that the material of the outer cover 30 attract and wick fluid so as to capture the fluid upon contact and then distribute it along/across the surface area of the underlying absorbent material 32, it will also be desired that the absorbent material 32 be able draw the fluid from the outer cover, i.e., that the outer cover not have a greater affinity for/tendency to retain the fluid therewithin, rather than surrender it to the absorbent material 32 (where it will, desirably, be stored for the duration of use of the tampon). Thus, it may be desired that the nonwoven web material forming the outer cover 30 be composed of a material or combination of materials that will cause the outer cover 30 to wick fluid therealong, but also to surrender it to the absorbent material 32. Accordingly, in examples in which rayon (a highly hydrophilic and absorbent fibrous material) constitutes a predominant weight proportion of the absorbent material 32, it may be desired that rayon constitute a lesser weight proportion of the nonwoven web material forming outer cover 30. In particular examples, a predominant weight proportion of the absorbent material 32 may be rayon, and nonwoven web material forming outer cover 30 may be composed of a blend of rayon, cotton, or fibers spun from thermoplastic polymer(s), wherein the weight proportion of rayon is no greater than 67 percent, more preferably no greater than 60 percent, and even more preferably no greater than 54 percent. Toward this objective, the weight ratio of the rayon fiber to spun thermoplastic polymer fiber, or other fiber, may be from 33:67 to 67:33, more preferably from 40:60 to 60:40, and even more preferably from 46:54 to 54:46. In particular examples the thermoplastic polymer fiber may be spun from a polymer that is ordinarily hydrophobic, and selected for attributes including smoothness (low friction) and softness (pliancy) against skin and tissues. Suitable examples include polypropylene, polyester, polyethylene terephthalate (PET), polyethylene, and combinations thereof. The combination of hydrophobicity and other attributes of the polymeric fibers, with the hydrophilicity of rayon fibers, will impart desirable wicking, structural and softness characteristics to the outer cover material, while reducing the overall hydrophilicity of the nonwoven web material, so that it will readily surrender wicked fluid to the absorbent material 32 adjacent thereto.

The fiber components of the nonwoven web material forming the outer cover 30 may be physically combined and blended, consolidated and bonded in any suitable fashion to form a cohesive nonwoven fabric material. However, it has been found that forming a web by creating a matt of blended component fibers in an airlaying or carding process, following by an entanglement process in which fibers of the matt are displaced and entangled so some extent along the z-direction, provides a web that better wicks fluid along the z-direction, as compared to a web that is not so processed. Z-direction entanglement may be imparted via processes such as, but not necessarily limited to, needling (or needle punching) and hydroentangling (as in a spunlace process). In a particular example, outer cover 30 may be formed of a nonwoven web material of which approximately 50 percent by weight is rayon fiber, and approximately 50 percent by weight is PET fiber, wherein the component fibers are carded and then hydroentangled. The web may have any suitable basis weight, but in order to balance competing objectives of mechanical strength and stability for purposes of maintaining structural integrity in processing, and suitable wicking and fluid penetrability characteristics, and material cost, it may be desired that the material be manufactured to have a basis weight of 15 gsm to 55 gsm, more preferably 25 gsm to 45 gsm, and even more preferably from 30 gsm to 40 gsm. In other examples in which processing equipment permits, a spunbond nonwoven web material spun from synthetic polymer fibers may have superior mechanical (tensile) strength per unit basis weight because the fibers are continuous rather than short/staple in length, and the spunbond material used may be of a lower basis weight, for examples, from 10 gsm to 30 gsm, more preferably from 15 gsm to 25 gsm, and even more preferably from 17 gsm to 22 gsm. In a particular nonlimiting example, outer cover 30 may be formed of a nonwoven spunbond material having a basis weight of 15 to 25 gsm, including (or even including, substantially all) fibers spun of polypropylene, and suitably treated so as to be rendered hydrophilic.

Figure 7:
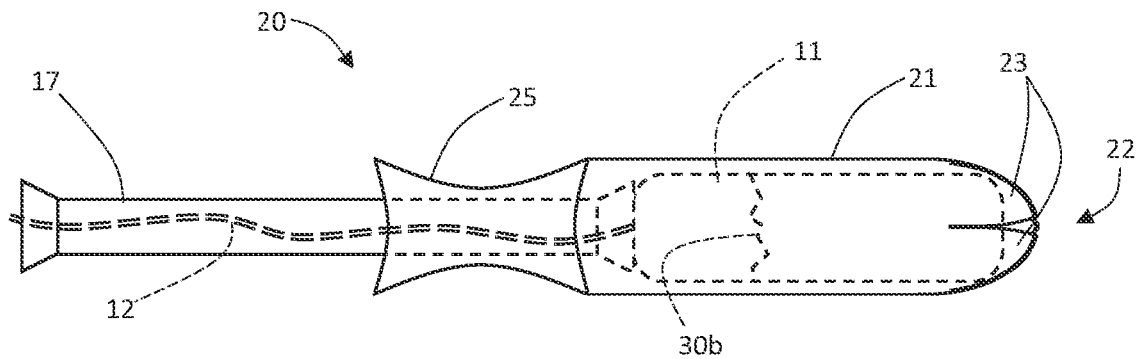
FIG. 7 is a schematic longitudinal/side view of a tampon product including an applicator, depicted prior to ejection of the tampon from the applicator.
Figure 8:
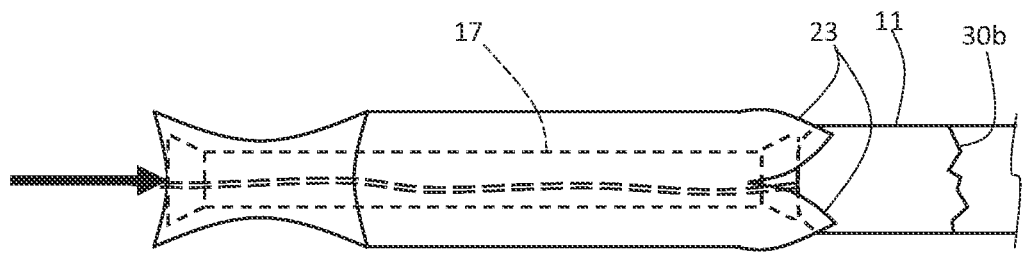
FIG. 8 is a schematic longitudinal/side view of a tampon product including an applicator, depicted during ejection of the tampon from the applicator.

In examples in which the pledget 11 is manufactured initially along a machine direction MD perpendicular to the longitudinal direction in the finished product (as suggested in FIG. 2), a continuous strip of batt, or other assembly, of absorbent 32, having a cross direction CD dimension approximately corresponding to the finished length PL of the pledget, may be conveyed along/together with a suitably sized web of material to form outer cover 30, through suitable web folding/wrapping plow equipment to fold and wrap the outer cover material about the absorbent material. Following subsequent cutting away of the individual pledgets from the continuous wrapped structure in cuts along the cross direction CD that form side edges 18, the wrapped/covered pledget can be imparted with a configuration reflected in, by way of non-limiting examples, FIGS. 3A-3C. It will be noted that the material forming outer cover 30 is depicted wrapped about the absorbent material such that overlapping portion 30a terminates at overlapping edge 30b, which is oriented rearwardly. Referring to FIGS. 7 and 8, this configuration may be particularly desired in examples in which the finished, compressed tampon is to be provided to the consumer inside an applicator 20 having a front end 22 defined by a radially-arranged group of flexible, closed petals 23. Many current applicators are provided in this general configuration, including a hollow barrel portion 21, a grip portion 25 and a hollow ejection plunger 17, which is configured to contain the withdrawal cord 12 within its hollow interior, and to slide, in telescope fashion, coaxially within grip portion 25 and barrel portion 21. Prior to application, pledget 11 of the new tampon is contained in barrel portion 21. Barrel portion has a front end 22 defined by the petals 23, which are biased (via the manner of their manufacture) to remain in a closed position as depicted in FIGS. 7A and 7B. In the closed position, petals 23 serve to retain the pledget within the barrel portion and to protect it from contamination, prior to use. When a user wishes to apply the tampon, she may grasp the grip portion 25 and insert the applicator, front end first, into the vaginal cavity to a suitable position, and then depress the plunger 17 along the direction of the large arrow (shown in FIG. 8) to push the tampon out the front end 22 of the applicator. As the forward end of the pledget 11 is urged against them as a result of longitudinal force exerted on the plunger 17, the petals 23 flex outwardly to expand an opening in the barrel portion at the front end 22 and allow the pledget to pass forwardly therethrough. Because the petals are biased to remain in the closed position, as they are forced outwardly, their forward tips will drag along the outer surface of the pledget 11 as it moves in a longitudinal direction through the opening. Thus, it may be desirable that overlapping edge 30b of outer cover 30 be oriented rearwardly as shown in FIGS. 3A-3C (rather than forwardly) so that it cannot be peeled back by the tips of the petals 23 as they drag along the surface of the pledget during ejection of the tampon from the applicator. Following ejection of the tampon from the applicator 20, the user withdraws the applicator, leaving the tampon 11 in place within the vaginal cavity.

The pledget 11 may have any suitable size, shape and thickness that will both provide a suitable quantity of absorbent material and resulting absorption capacity, while permitting compression into a self-sustaining form of a size and shape suitable for easy and comfortable insertion. An uncompressed, opened size similar to those of conventional currently available tampons has been found to work well. A typical size for an uncompressed pledget may be from about 2 cm to about 9 cm in longitudinal length and from about 3 cm to about 8 cm in lateral width, including any combination of length and width within those ranges, in combination with an uncompressed thickness anywhere from about 1 cm to about 3 cm. Total basis weight for a flat, uncompressed and open pledget, may be from about 150 g/m2 to about 1,400 g/m2, calculated as the weight of the pledget divided by the largest surface area on one side of the pledget. Optionally, a pledget 11 that is shorter and wider than the ranges given above may also be desired in some circumstances to promote relatively greater swelling/expansion in a lateral or radial direction during use.

A withdrawal cord 12, configurations of which are depicted in the figures, is preferably joined to the pledget to facilitate withdrawal of the tampon from the vagina following a desired duration of use. The withdrawal cord 12 may have an attached portion 12a attached to the pledget 11 and a free portion 12b extending beyond the rearward end 17 thereof (and also rearwardly beyond the rearward edge of the wicking member 15). In other examples, the withdrawal cord may be integral with the pledget, or an extension of a structural component of the pledget, such as of an outer cover as described above. In some examples the withdrawal cord 12 may be integral with and/or an integral extension of a wicking member 15.

In a particular example, the withdrawal cord 12 may be a separate section of cord, string, yarn, ribbon, knitted cord or strip of woven or nonwoven fabric formed separately of the components of the pledget and wicking member, and then attached by any suitable mechanism to the pledget and/or to the wicking member.

The attachment mechanism may include sewing, adhesive attachment, thermal or pressure bonding, through-pledget punching, penetration and/or looping of the withdrawal cord material about structure(s) of the pledget or portions thereof, or any combination of these. An attached portion 12a of the withdrawal cord 12 may be attached or joined to any suitable location on the pledget 11, although it may be preferable that the attachment/joining location be substantially laterally centered on the pledget and proximate to, or include a location proximate to, the rearward end 17 of the pledget, so that tensile withdrawal force in the cord, exerted by the user, acts predominantly on the rearward end of the pledget and thereby does not tend to substantially rotate or reorient the pledget within the user's body during withdrawal. In the example shown in FIGS. 2 and 3A-3C, an attached portion 12a of the withdrawal cord 12 is joined to the pledget 11 along the length of the pledget 11, and free portion 12b trails free beyond the rearward end 17 of the pledget 11 and rearward edge 15c of the wicking member 15. The withdrawal cord 12 may be attached to the tampon pledget 11 while the pledget 11 is still uncompressed, as shown in FIG. 2. The withdrawal cord 12 may be attached along substantially the entire length of one of the major surfaces 35, 36 of the pledget 11.

Figure 5:
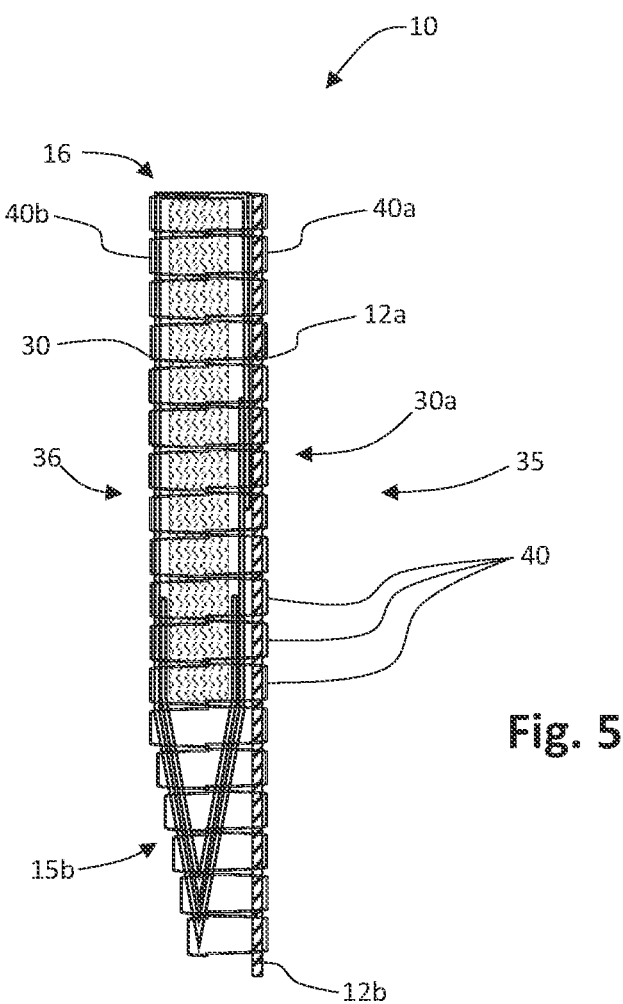
FIG. 5 is a schematic longitudinal cross section of components of the tampon shown in FIG. 2, taken through line 3A-3A in FIG. 2, shown with the components slightly separated for visibility, and depicting a configuration of stitches that may be included to hold the components together (for purposes of visibility the stitches are depicted in a loose, separated condition, rather than being depicted as drawn together tightly as they would appear in an actual product).

To minimize chances of failure of the attachment between the withdrawal cord 12 and the pledget (i.e., separation) during withdrawal, it may be desired that the withdrawal cord be directly or indirectly attached along substantially the entire length of the pledget, thereby diffusing tensile withdrawal force exerted by the user, by distributing it over the length of the pledget. Referring to FIG. 5, to further minimize chances of failure of the attachment, it may be desired that the attachment mechanism include a longitudinal line of lockstitches 40 in which stitches 40 entirely penetrate the withdrawal cord 12 and the pledget (through both sides), thereby connecting and affixing the withdrawal cord through a substantial portion of the structure of the pledget, rather than only to an outer surface thereof. Such attachment further diffuses withdrawal force through the main body/structure of the pledget. In other examples, a length of withdrawal cord stock may be threaded through a portion of the body/structure of the pledget (e.g., through a hole punched therethrough (not shown)), looped around and doubled to create pair of trailing portions (not shown). In still other examples, a length of withdrawal cord stock may be looped around a substantial portion of the pledget body without punching, and doubled to create pair of trailing portions (not shown.) The trailing portions of the pair may be tied and knotted or otherwise affixed together. These latter two approaches also may be employed to provide a secure connection between the pledget and the withdrawal cord.

Where lockstitching is used to attach the withdrawal cord to the pledget, it may be desired that the line of stitches 40 extend longitudinally along substantially the entire length of the withdrawal cord 12. In examples in which the withdrawal cord 12 is formed of a section of twisted, braided or knitted strands or fibers, lockstitching that traverses substantially the entire length of the withdrawal cord may be desired because the thread strands forming the stitches through the cord are effectively intertwined with component fibers and/or strands of the cord, and can thereby function to substantially prevent the cord from unraveling from its cut ends. Herein, a line of "lockstitching" means a line of stitches formed of at least two strands of thread 40a, 40b disposed on opposing sides of the body(ies) to be stitched together, wherein stitches are sequentially formed as each thread meets and loops around the other, via passage through the body(ies) by one or both threads, at suitable intervals corresponding to the desired size of the stitch. In some examples, a first thread may be sequentially passed through the body(ies) to meet the second thread via use of an appropriate sewing needle, while the second thread is looped about the first thread by operation of a looper. Chainstitching consisting of two threads as described above is included within the definition. A non-limiting example of lockstitching may be seen in FIG. 5, depicting a longitudinal cross section through a wicking member 15 and withdrawal cord 12, wherein these two components are held together by a longitudinal line of lockstitching with stitches 40 formed by front thread 40a and rear thread 40b. FIG. 5 depicts ISO #301 type lockstitching, as specified by the International Organization for Standardization, ISO 4519:1991, as an example. Other types of lockstitching may be preferred in some circumstances, for example, ISO #401 type chainstitching, which may further enhance the stitches' ability to resist unraveling themselves, and prevent unraveling of the stitched withdrawal cord and/or wicking member, at cut forward and/or rearward ends thereof.

In some circumstances in which the line of lockstitching exists substantially along the length of the free portion 12b of the withdrawal cord 12, it may be desired that the threads used to form the line of lockstitching be made of a suitably hydrophobic fiber material, or fiber material treated to be suitably hydrophobic, so that the lockstitching thread is unlikely to wick fluid along the trailing portion of the withdrawal cord. In some examples the lockstitching thread may be formed of or include cotton fiber, processed or treated to be suitably hydrophobic. In some examples the lockstitching thread may be formed of or include polyester fiber (which in some formulations may be inherently somewhat hydrophobic). In some examples the lockstitching thread may be formed of or include a blend of cotton fiber and polyester fiber, wherein the cotton fiber may be processed or treated to be suitably hydrophobic.

The tampon 10 may also be provided with multiple withdrawal cords 12. For example, two withdrawal cords 12 may be attached down the length of the pledget 11 and extend from the withdrawal end thereof. In such an instance, the wicking member, may be joined to one or both of the withdrawal cords 12.

Especially when the wicking member 15 is joined to the withdrawal cord 12, the withdrawal cord 12 is preferably non-absorbent along at least the location of such attachment. As used herein, the term "non-absorbent" refers to a structure formed predominantly of suitably hydrophobic materials such that upon contact with aqueous fluid such as menstrual fluid, it does not tend to attract, take in, wick or retain any substantial quantity of the fluid within its structure. In some examples it may be desired that the material(s) forming substantially the entire withdrawal cord 12 be hydrophobic, so that the withdrawal cord does not attract or wick menstrual fluid along its trailing portion 12b, potentially out to its trailing end. The materials comprising the withdrawal cord may be inherently non-wettable or hydrophobic, or they may be treated to provide such properties. For example, a suitable wax may be applied to the withdrawal cord 12 to decrease or eliminate wicking tendency. Other means for providing a material suitable for use as a withdrawal cord 12 which is non-absorbent and/or non-wicking are known in the art. For example, U.S. Pat. No. 5,458,589 describes one approach. However, the withdrawal cord 12 need not necessarily be non-wicking along its entire length, even if a non-absorbent withdrawal cord is desired. For example, it may be desirable to provide a withdrawal cord 12 in which at least a portion of the cord has a tendency or capability to wick deposited fluid upwardly toward the rearward end 17 of the pledget and into the structure thereof.

The withdrawal cord 12 need not have uniform properties throughout its length. For example, the portion of the withdrawal cord attached to or nearest the pledget 11 may be manufactured and/or treated so as to have wicking capability, while the free portion 12b of the withdrawal cord 12 may be manufactured and/or treated so as to not have wicking capability. Other properties such as hydrophilicity/hydrophobicity, density, capillary size, width, thickness, and the like may also vary along the length of the withdrawal cord 12.

The withdrawal cord 12 may be formed of a strand or strands of component yarn or thread material. In some examples the yarn or thread material may be formed of cotton fiber, cotton fiber processed or treated to be suitably hydrophobic, other natural plant-based fiber which may be processed or treated to be suitably hydrophobic, or polyester, or a combination or blend thereof.

The component yarn or thread may be knitted, twisted or braided to form the withdrawal cord stock. For maximized tensile strength per unit decitex of the withdrawal cord stock, it may be desired that the component yarn or thread be of twisted or braided construction (rather than of knitted, woven or other construction).

Tampons of the type and configurations contemplated herein may also have or include any combination of features described in U.S. Application Ser. No. 62/780,388, filed on Dec. 17, 2018 by Strong et al. and/or U.S. Application Ser. No. 62/834,427, filed on Apr. 16, 2019 by Strong et al.

Wicking Member

The tampon 10 also may be provided with a wicking member 15. Herein, a "wicking member" is a portion of the tampon, not including the withdrawal cord, that trails from the rearward end 17 of the pledget 11. An overlapping portion 15a of the material forming the wicking member may be present along a portion or length of the pledget 11, and the material forming the wicking member may have a trailing portion 15b extending or trailing by a suitable length from the rearward end 17 of the pledget 11. The wicking member 15 may be separate from, or joined to, the withdrawal cord 12 along a portion or all of their respective lengths. As will be discussed below, the wicking member 15 may be provided, following insertion of the tampon at a suitable location within the vaginal cavity, to extend rearward of (trail) the rearward end of the pledget, further down the vaginal cavity toward the introitus, where it can be in position to contact menstrual fluid that may be present below the pledget, and attract and wick liquidous components thereof up to the pledget 11.

The wicking member 15 may be formed of a suitable configuration of fibrous material having suitable fluid handling properties and tensile strength. It may be desired that the wicking member be formed separately of the withdrawal cord, and of one or more material(s) distinct from the one or more materials forming the withdrawal cord. As discussed above, in some examples it may be desired that the material(s) forming the withdrawal cord be suitably hydrophobic, to reduce or avoid wicking of fluid along the withdrawal cord. This is contraindicated by the requirements for the wicking member as discussed herein, and it may be desired that hydrophobic fibrous components of the withdrawal cord not be present within the structure of the wicking member, where they can contribute to obstructing or interrupting wicking. Accordingly, it may be desired that the respective structures of the wicking member and withdrawal cord not be coaxial and/or not be intermingled. Rather, as suggested in the figures, the wicking member and the withdrawal cord may be arranged in contact with each other (or not) along a substantially parallel, non-coaxial configuration; see, e.g., FIGS. 3A-3C, depicting such a non-coaxial configuration, where the longitudinal axes of the wicking member 15 and withdrawal cord 12, respectively, are not the same (although they may be parallel).

The ability and tendency of a fibrous structure to draw in and transport (herein, "wick") aqueous fluid against the influence of external forces acting on the fluid (such as gravity) is a function of several features of the structure. These include the extent of hydrophilicity of the surfaces of the fibers; the extent of capillarity within the structure (where capillarity relates to the number and average size and volume of interstitial spaces constituting potential fluid passageways between and among the fibers, resulting from the extent and manner of fiber consolidation in the structure); the complexity of the fibers' surface geometry(ies); and the extent to which the structure has already drawn in and retains (i.e., has absorbed) fluid (i.e., saturation level). Capillarity of a fibrous structure relates to the amount of fiber surface area that is present within the structure, per unit volume of the overall structure, and to the density of consolidation of the fibers in the structure, which affects the size and volume of the interstitial spaces or fluid passageways. The size and volume of the interstitial passageways affect the degree to which the aggregate attractive pull of the hydrophilic fiber surfaces in contact with the fluid can overcome forces that resist it, i.e., surface tension of the fluid and external forces such as, e.g., gravity or pressure differential. For example, for a structure formed of a given fiber composition, interstitial passageways which are too large can make the structure ineffective at wicking upward against gravitational pull because there is an insufficient aggregate area of hydrophilic fiber surfaces in contact with the fluid to create attractive pull sufficient to overcome gravitational pull acting on the relatively large fluid volume and mass in the relatively large passageways, and surface tension of the fluid mass itself tending to resist separation into smaller fluid volumes. On the other hand, interstitial passageways which are too small and/or insufficient in aggregate volume such that, while effective at moving fluid in small volume, can be physically restrictive with respect to wicking volume flow rate. For a given type of hydrophilic fibers, there will be an optimum capillarity in a structure formed of them, at which wicking potential is maximized.

Further, the composition of human menstrual fluid differs from pure water or typical saline test solution in ways (e.g. surface tension) that cause the fluid to behave differently than water or saline solution with respect to wicking structures and absorbent structures. For this reason, a given structure may more readily and/or rapidly wick or absorb a greater quantity of water or saline than menstrual fluid, and vice versa. For purposes herein, wicking and absorption of human menstrual fluid, relevant compositional aspects of which are herein deemed suitably approximated by defibrinated sheep's blood under conditions described herein, are of interest and focus. For a structure formed of a given fiber composition there will be a level of fiber consolidation that optimizes capillarity and wicking performance under these conditions.

Wicking and absorption are relatively complex phenomena and can be difficult to precisely measure and characterize for many types of structures. However, it may be observed, generally, that: (1) between two dry fibrous structures formed of identically composed fibers having similar hydrophilicity, the structure with the more optimal capillarity will have the greater wicking performance; (2) between two dry fibrous structures formed of fibers of differing compositions but having similar capillarity, the structure formed of the fibers having greater hydrophilicity will have the greater wicking performance; (3) between two wetted fibrous structures having similar capillarity, formed of fibers of the same composition and having similar hydrophilicity, the structure holding the lesser quantity of aqueous fluid per unit structure volume will have the greater wicking potential. Between two differing first and second fibrous structures that are placed in contact with each other, the first structure will draw fluid from the second structure if the first structure has a combination of hydrophilicity, capillarity and level of fluid content (saturation level) per unit structure volume that impart to it greater wicking potential than the second structure. Conversely, if the first structure has lesser wicking potential than the second structure, the first structure will not draw fluid from the second structure.

Thus, it may be desired that the component fibrous material of the wicking member 15 have a combination of fibers with hydrophilic surface properties, and optimized capillarity, to promote wicking of fluid therealong, but at the same time, not have, or not be assembled in a configuration having, a combination of capillarity and hydrophilicity that render it more likely to attract and retain menstrual fluid against the wicking potential of the absorbent material(s) 32 of the pledget 11. It is preferred that the material of the wicking member serve to wick fluid to the pledget, but that the material(s) of the pledget have greater wicking potential and absorbency so as to be effective at drawing menstrual fluid from the wicking member over the expected duration of use of the tampon.

In some examples the wicking member may be formed of fibrous material(s) similar to those used to form the pledget, e.g., rayon fibers, absorbent cotton fibers or any combination thereof. In such examples the fibrous materials forming the wicking member and pledget should be configured such that the body of the wicking member has less wicking potential than the pledget. The wicking potential of the wicking member can be adjusted by the selection of material of which it is formed, for its relative level of fiber surface hydrophilicity and its relative capillarity. Capillarity may be adjusted by the manner in which the fibers forming the wicking member are consolidated and densified within the structure. As suggested in FIGS. 3A-3C, the wicking member 15 may be formed in part or entirely of the same nonwoven web material used to form the outer cover 30, or even a continuous, integral extension thereof.

It has been discovered that a non-hydrophilic (i.e., hydrophobic) fibrous material can be effectively treated and configured to serve the desired wicking function while in most circumstances having less affinity for the fluid than typical pledget materials (i.e., rayon fiber and/or cotton fiber). Spun polymeric synthetic fibers that are ordinarily hydrophobic, such as spun polypropylene fibers, may be treated, e.g., via application of a suitable surfactant finish, to render their surfaces hydrophilic. Since such fibers typically have simple and/or smooth and non-porous surface geometry, however, the fiber surfaces themselves do not substantially contribute to capillarity, and bundles or assemblies of such fibers will have substantially less wicking potential (and tendency to retain the fluid) than bundles or assemblies of more complexly-shaped hydrophilic fibers such as rayon, cotton, or other natural plant-based fibers. Accordingly, in some examples it may be desired that the wicking member be formed of fibrous material that includes spun thermoplastic polymer material such as polypropylene, polyester, polyethylene terephthalate (PET), polyethylene, polyamide (e.g., nylon) or other thermoplastic polymeric material, or any combination thereof. To enhance wicking performance, the wicking member may also include a more hydrophilic and/or more absorbent fibrous material such as cotton fibers, other cellulose and/or plant-based fibers, or even rayon fibers. In some examples the wicking member may be formed of a blend of plant-based (e.g., cotton) and/or rayon fibers, and fibers spun from thermoplastic polymer(s). As described above for the material used to form the outer cover 30, in particular examples the thermoplastic polymer fiber may be spun from a polymer that is ordinarily hydrophobic, and selected for attributes including smoothness (low friction) and softness (pliancy) against skin and tissues. Suitable examples include polypropylene, polyester, polyethylene terephthalate (PET), polyethylene, and combinations thereof. The combination of hydrophobicity and other attributes of the polymeric fibers, with the hydrophilicity of cotton and/or rayon fibers, will impart desirable wicking, structural and softness characteristics to the outer cover material, while reducing the overall hydrophilicity of the nonwoven web material, so that it will readily yield wicked fluid to the absorbent material 32 in the pledget.

For a more detailed description of hydrophilicity and contact angles see the following publications which are incorporated by reference herein: The American Chemical Society Publication entitled "Contact Angle, Wettability, and Adhesion," edited by Robert F. Gould, and copyrighted in 1964; and TRI/Princeton Publications, Publication Number 459, entitled "A Microtechnique for Determining Surface Tension," published in April 1992, and Publication Number 468 entitled, "Determining Contact Angles Within Porous Networks," published in January, 1993, both edited by Dr. H. G. Heilweil.

While a tampon with a wicking member may absorb some menstrual fluid into the wicking member and may even wick fluid to the pledget to some extent, it is believed from research that the effectiveness of the combination may not be meaningfully noticeable to a user unless its ability to capture and wick fluid through the wicking member up to the pledget exceeds a particular value for Wicking as set forth and described herein. A combination of materials described herein, used to constitute and configure a tampon product, may be selected and assembled as described to provide a tampon that will wick at least 1.2 grams, more preferably at least 1.5 grams and even more preferably at least 3.2 grams of test fluid up through the wicking member as measured using the Wicking Measurement method herein. Information herein and also as known in the art is sufficient to enable one to select materials for the pledget and for the wicking member to achieve these levels of wicking. If the material of the wicking member has an insufficient combination of suitable hydrophilicity and capillarity, it will be unable to attract and wick menstrual fluid upwardly to the pledget to the levels specified herein, under the conditions of the measurement method (which are designed to approximate the orientation of the tampon and pressure to which its materials are subjected when the tampon is in use, disposed in the vaginal cavity). For this reason, a wicking member formed of polymeric fibers, for example, that have not been suitably processed or treated to render them suitably hydrophilic, have insufficient longitudinal directional orientation, and/or are too loosely or too densely consolidated, will be ineffective. On the other hand, if the material of the wicking member has a combination of hydrophilicity at a suitable level and capillarity that makes it have a greater affinity for fluid contained therein than can be overcome by the wicking potential of the pledget, the pledget will be unable to draw fluid away and out of the wicking member, and once saturated, the wicking member will cease wicking. For this reason, a wicking member formed primarily of, for example, completely scoured cotton fibers, and/or rayon fibers (which have a high affinity for aqueous fluid and therefore form structures that are relatively highly absorbent), may be unsatisfactory. On the other hand, a blend comprising, for example, no greater than about 75 weight percent, more preferably no greater than about 63 weight percent, and even more preferably no greater than about 50 weight percent cotton, rayon, or any combination thereof, with the balance constituted by synthetic fibers such as polyethylene, polyethylene terephthalate (PET), polypropylene, polyester, polyamide, or any combination thereof, may impart suitable wicking properties but still yield fluid up to a pledget formed predominantly of cotton, rayon (or viscose, or lyocell), or a combination thereof, and suitably structured. The ability of the pledget to draw fluid from the wicking member may be further enhanced by processes and configurations described in U.S. provisional patent application Ser. No. 62/683,661. A balance between wicking potential of the pledget and wicking potential of the wicking member may be identified to meet the wicking levels specified above. It has been learned that a level of measured wicking at one or more levels specified above is greater than that achieved by currently available tampons that include wicking structures. It is believed that a level of measured wicking at levels specified above represents improvement in the performance of tampons with wicking structures, in preventing bypass leakage or leakage of residual fluid in the vaginal cavity present following removal of a used tampon. Using combinations of materials described herein, the inventors have achieved measured wicking as high as 3.5 grams, although it is contemplated that greater levels as high as 3 grams, 4 grams or even 5 grams may be achievable through experimentation, using suitable combinations of materials and configurations identified herein or otherwise known to the person of ordinary skill in the art.

A single layer or ply of web material having a suitable basis weight may be used to form wicking member 15. However, it has been discovered that a multi-ply/multi-layer structure that may be formed by folding a relatively lower basis weight web material over on itself, along fold lines, in a manner that appears to increase wicking efficacy as compared with a single-layer structure having a basis weight comparable to that of the multi-layer/multi-ply structure. Without intending to be bound by theory, it is believed that the several plies or layers in folded configuration provide added, alternative fluid passageways with regions having variations in size and capillarity, such that alternative fluid passageways are presented around regions in which wicking may be impaired by, e.g., regions of excessively high or low fiber density/compaction. Further, it has been observed that folding such material from a rolled supply may be accomplished efficiently on a manufacturing line, using suitable web folding plows. The material may be folded in various configurations to form a wicking member having at least two, more preferably at least three, and even more preferably at least four layers, as suggested in FIGS. 3A-3C. To avoid over-densification of fibrous structure that may negatively compromise capillarity of the wicking member, however, it may be desired that wicking member 15 have no more than six, preferably no more than five, component material layers.

From FIGS. 3A-3C, it can be appreciated that the trailing edge 15c of wicking member 15 may be defined by a fold in the outermost layer of material(s) forming the wicking member. Such a fold may be formed during manufacture, using suitable web folding equipment. Such a fold, rather than cut edges, give the trailing edge 15c of the wicking member a neater appearance, and reduces occurrence of fraying of the material and shedding of fibers, as may be present along a cut edge.

The wicking member 12 may have any suitable length, but its trailing portion 15b (the portion extending rearward of rearward end 17 of pledget 11) is preferably shorter than the trailing portion of the withdrawal cord 12. The trailing portion of the wicking member 15 should not be long enough to extend through the introitus when the tampon 10 is fully inserted and properly positioned within the vaginal cavity. Although dimensions of the vaginal cavity vary among individual users, it may be desired for most users that the trailing portion 15b of the wicking member 15 should have a length WL no greater than 60 mm, more preferably no greater than 50 mm, even more preferably no greater than 40 mm, and still more preferably no greater than 30 mm, and preferably no less than 10 mm, more preferably no less than 15 mm, and even more preferably no less than 20 mm. (For purposes herein, the length of the trailing portion is measured with the trailing portion held in a straightened position, but in a relaxed condition, i.e., not under longitudinal tension greater than 5 gf).

In order to ensure that an adequate portion of the surface area(s) of the material(s) forming wicking member 15 are exposed to direct or indirect facing contact with the pledget (for purposes of facilitating transfer of fluid from the wicking member to the pledget), it may be desired that at least three layers of the material forming the wicking member 15 have an overlapping portion 15a overlapping the pledget, by a minimum overlapping length MOL that is at least 2 percent, more preferably at least 3 percent, and even more preferably at least 4 percent, of the total length PL of the pledget. In a particular example, the overlapping and trailing portions of the material(s) forming the wicking member 15a, 15b may be approximately equal in length. It may also be preferred that the overlapping portion of the material(s) forming the wicking member overlap the pledget along a length that is at least 2 mm, and more preferably at least 3 mm, and even more preferably at least 4 mm. It will be appreciated from FIGS. 3A-3C that, when the material forming the outer cover 30 also integrally forms the wicking member 15, it may overlap substantially the entirety of the length of the pledget PL.

To enhance unitized structural integrity of the tampon, it may be desired that the material(s) forming the wicking member 15 be lockstitched to the pledget, in a manner such as described above. In some examples the withdrawal cord 12 and the wicking member 15 may be lockstitched together to the pledget, via the same configuration/line of lockstitches 40 (see FIG. 5). In such configuration, it may be desired that the material(s) forming the wicking member be disposed in direct contact with the pledget, and preferably that the material(s) forming the wicking member be disposed between the pledget and with the withdrawal cord, to provide for direct contact and fluid transfer between the wicking member and the pledget, unobstructed by the (e.g., hydrophobic) structure of the withdrawal cord. In some examples, however, the material(s) forming the wicking member 15 may be attached to the pledget 11 by a mechanism differing from that attaching the withdrawal cord 12 to the pledget 11, and may also be physically separated from the withdrawal cord 12 at or along location(s) of attachment on the pledget. In some examples, the material(s) forming the wicking member 15 may be attached to the pledget 11 by adhesive bonds, by thermal compression or ultrasonic bonds (in which respective material(s) of the wicking member and of the pledget are fused or welded together) or may be stitched to the pledget by stitches separate from stitches attaching the withdrawal cord to the pledget 11. In the examples depicted in FIGS. 3A-3C and 5, the absorbent material 32, outer cover 30 and wicking member 15 (the material of which may be partially or entirely continuous and integral with the material forming the outer cover 30), may be held together substantially only by the stitches 40, such that other bonding mechanisms are not necessary, or only minimally included for, e.g., temporary manufacturing/assembly process needs. Omission of any substantial bonding mechanism such as thermal bonds or adhesive bonds avoids occluding areas of contact between the absorbent material 23 and the material(s) forming the wicking member 15, which can interrupt fluid transfer therebetween. (Herein, a "substantial bonding mechanism" between the absorbent material 32 and the material(s) forming the wicking member 15, is one in which more than 5 percent of that portion of the surface area of the absorbent material 32 in contact with material(s) forming the wicking member 15 is occupied by melted or fused polymer or applied adhesive bonding the absorbent material to the material(s) forming the wicking member 15.)

In some further examples, one or more threads used to form stitches 40 attaching the material(s) forming the wicking member 15 to the pledget 11 may be selected for suitable tensile strength and hydrophobicity such that they may be extended beyond the trailing rearward end of the wicking member by a suitable length, and by themselves serve as the withdrawal cord. This configuration eliminates the need for, and expense and complexity associated with including, a separate withdrawal cord. Where two or more stitching threads are used to lockstitch the material(s) forming the wicking member to the pledget, they may be twisted, braided or otherwise suitably intertwined or combined into a singularized cord configuration in a trailing portion extending rearwardly from the wicking member.

It may be desired that any one or more of the material(s) used to form the wicking member 15 be tinted or pigmented to impart the wicking member with a color that visibly contrasts with the color(s) of the materials forming the pledget, outer cover and/or withdrawal cord. This may be deemed useful for visually signaling to the user that a differing material is present in the wicking member, suggesting a functionality distinct from that of the withdrawal cord. In connection with appropriate information on, or associated with, packaging for the tampon product, such tinting or pigmenting can advantageously serve to remind the user that the wicking member is present to provide supplemental protection against leakage. When the pledget and/or materials constituting the pledget have a substantially white color (which is, for example, the natural color for suitably processed, undyed cotton, and is believed to be preferred by many consumers because it connotes purity, cleanliness, sanitation and/or freshness), it may be desired that the material(s) constituting the wicking member are imparted with a non-white color that not only visibly contrasts with the color of the pledget, but also visibly contrasts with color(s) of areas of a pledget as stained by menstrual fluid as it may appear immediately following use. Thus, in some examples it may be preferred that the non-white color of the wicking member be selected from a range of colors that will visibly contrast with the color of the pledget, and with the color(s) of the pledget when stained by menstrual fluid, as it appears immediately following withdrawal of the tampon. This coloration feature may serve to provide the user with additional signal of the functionality of the wicking member. For purposes herein, "substantially white" means having CIE L*a*b* values when measured according to the Color Measurement Method set forth below, in which L* is ≥87, and the absolute values of each of a* and b* are ≤2. A wicking member color that visibly contrasts with the color of the pledget is any color that exhibits a ΔE*≥15 from the color of the pledget, measured according to the Color Measurement Method below. Techniques for imparting varying colors, and adjusting the depth thereof, to synthetic, semi-synthetic and natural plant-based fibers or filaments, or materials made therefrom (e.g., via use or inclusion of pigments, dyes or inks), are known in the art.

In an array of two or more packaged tampon products (herein "array" means two or more differing products of the same brand, marketed or appearing for sale simultaneously in the same or proximate respective locations (physical or online/virtual) (e.g., on the same or respective proximately located shelves within the same retail store)), differing wicking members can be included with tampons of differing features, for the purposes of functioning differently with the differing tampon products, signaling the differences in features to consumers, or a combination of both. In one non-limiting example, packaged tampons having a first absorption capacity may include wicking members imparted with a first color, while packaged tampons having a second, differing absorption capacity may include wicking members imparted with a second color visually distinguishable from the first color. For purposes herein, a second wicking member color is "visually distinguishable" from a first wicking member color when the second wicking member color exhibits a ΔE*≥5 from the first wicking member color, measured according to the Color Measurement Method below. Wicking members for an array of differing tampon products may differ not only in color, but in other characteristics such as material composition and/or absorbency/wicking characteristics, physical structure (e.g., braided, twisted, knitted, etc.), length, width, diameter, density, decitex or other dimension, location of attachment on the pledget, etc. The differing tampon products with respectively differing wicking members may be accompanied by associated packaging material imprinted with graphic/pictorial information, verbal information, or a combination thereof, that signals the differences in the respective products and/or wicking members.

A tampon as contemplated herein is believed to offer several advantages over prior art tampons. As noted previously, the incorporation of the wicking member 15 extends fluid capturing capability to lower regions of the vaginal cavity. Additionally, because the tampon can be manufactured by processes in which the wicking member is less compressed than the pledget 11, the material forming the wicking member can be available to immediately draw in fluid, without the need for re-expansion from a compressed state.

Tampons of the type and configuration(s) contemplated herein may be manufactured via the process described in U.S. Application Ser. No. 62/780,388, filed on Dec. 17, 2018 by Strong et al. and/or U.S. Application Ser. No. 62/834,427, filed on Apr. 16, 2019 by Strong et al.

To form a tampon ready for use, the tampon pledget 11 may be compressed and heat conditioned (which may include use of steam or elevated humidity) in any suitable conventional manner to impart it with a self-sustained form suitable for easy and comfortable insertion, which may be a cylindrical form. Pressures, temperatures and humidity conditions suitable for this purpose are known in the art. Typically, the pledget 11 is compressed in radial and/or lateral directions using any suitable means known in the art. While a variety of techniques are known and acceptable for these purposes, a modified tampon compressor machine available from Hauni Machines, Richmond, VA, is suitable. Non-limiting examples contemplated herein may be compressed primarily in the lateral direction (i.e., perpendicular to the longitudinal direction and z-direction).

The tampon 10 contemplated herein may be inserted digitally or via the use of an applicator. If the tampon 10 is to be configured for digital insertion, or for insertion from a generally cylindrical applicator, it may be desirable to form the pledget from a layer of absorbent material which has been rolled or otherwise formed into a cylindrical or capsule shape.

Any of the currently available tampon applicators may also be used for insertion of the tampon contemplated herein. Such applicators of typically a tube-and-plunger type arrangement and may be plastic, paper, or other suitable material. A compact type applicator can also be suitable. The applicator plunger may be depressed by the user to push the compressed pledget 11 out of the applicator while fitting around the wicking member 15.

Color Measurement

The total color difference (ΔE*) between a tampon pledget 11 and its wicking member 15 is calculated from the L*a*b* color values obtained for each respective portion of the tampon. Color analyses are made using a 0°/45° spectrophotometer with adjustable apertures capable of making standard CIE L*a*b* measurements in accordance with ASTM E1349. An example of a suitable spectrophotometer is the Labscan XE (available from Hunter Associates Laboratory, Inc., Reston, VA, or equivalent). All testing is performed in a room maintained at a temperature of 23° C.±2.0° C. and a relative humidity of 50%±2% and samples are conditioned under the same environmental conditions for at least 2 hours prior to testing.

If the tampon is provided in an application, the test sample is prepared by first removing the tampon 10 from the applicator in the manner the product is designed to effect ejection of the tampon 10 from the applicator. The pledget 11 is flattened out by gently opening it from its self-sustaining shape. Using a small pair of scissors to sever any stitching as necessary, or using freeze spray to deactivate any adhesive used to join them, gently separate and remove the wicking member 15 from the pledget 11, using care so as not to damage either component in the process. For each product tested, a total of 5 pledgets and 5 wicking members are prepared in this manner.

To measure color, calibrate and standardize the instrument per the vendor instructions using the standard white and black tiles provided by the vendor. Set the spectrophotometer to use the CIE L*a*b* color space with a D65 standard illumination, a 10° observer, a 0.125 inch area view, a 0.200 inch aperture, and the UV filter set to nominal. Place the pre-flattened pledget test sample over the aperture such that the entire aperture is covered by the pledget 11 on an area free of the withdrawal string 40. Place the standard white tile behind the pre-flattened pledget test sample, take a reading and record L*a*b* values as L2*a2*b2* to the nearest 0.01 units. Remove the pledget test sample from the aperture and replace it with the wicking member test sample. Ensure that the entire aperture is covered by the wicking member, minimizing the amount of withdrawal cord 12 present in the aperture's viewing area. Place the standard white tile behind the wicking member test sample, take a reading and record L*a*b* values as L1*a1*b1* to the nearest 0.01 units. Calculate the total color difference (ΔE*) between the pledget and the wicking member as follows:

$$\Delta E^* = [(L2^* - L1^*)2 + (a2^* - a1^*)2 + (b2^* - b1^*)2]^{1/2},$$

and record as ΔE* to the nearest 0.01 units.

In like fashion, repeat for a total of five measurements obtained on five different tampon pledget and wicking member samples. Calculate the arithmetic mean for ΔE* obtained from all five measurements and report to the nearest 0.01 unit.

Wicking Measurement

The ability of a tampon configuration with a wicking member to capture fluid in the wicking member, and wick and fluid to the pledget, may be measured using this Wicking Measurement method. A known quantity of test fluid is delivered at a constant rate over a specified amount of time to a portion of the wicking member 15 inside a pressurized wicking chamber. The quantity of fluid absorbed by the tampon 10 is determined and reported as Total Uptake. All measurement is performed in a laboratory maintained at 23° C.±2 C.° and 50%±2% relative humidity. The measurement equipment as described herein is configured to approximate the pressure to which a tampon is subjected inside the body during actual use.

Figure 9A:
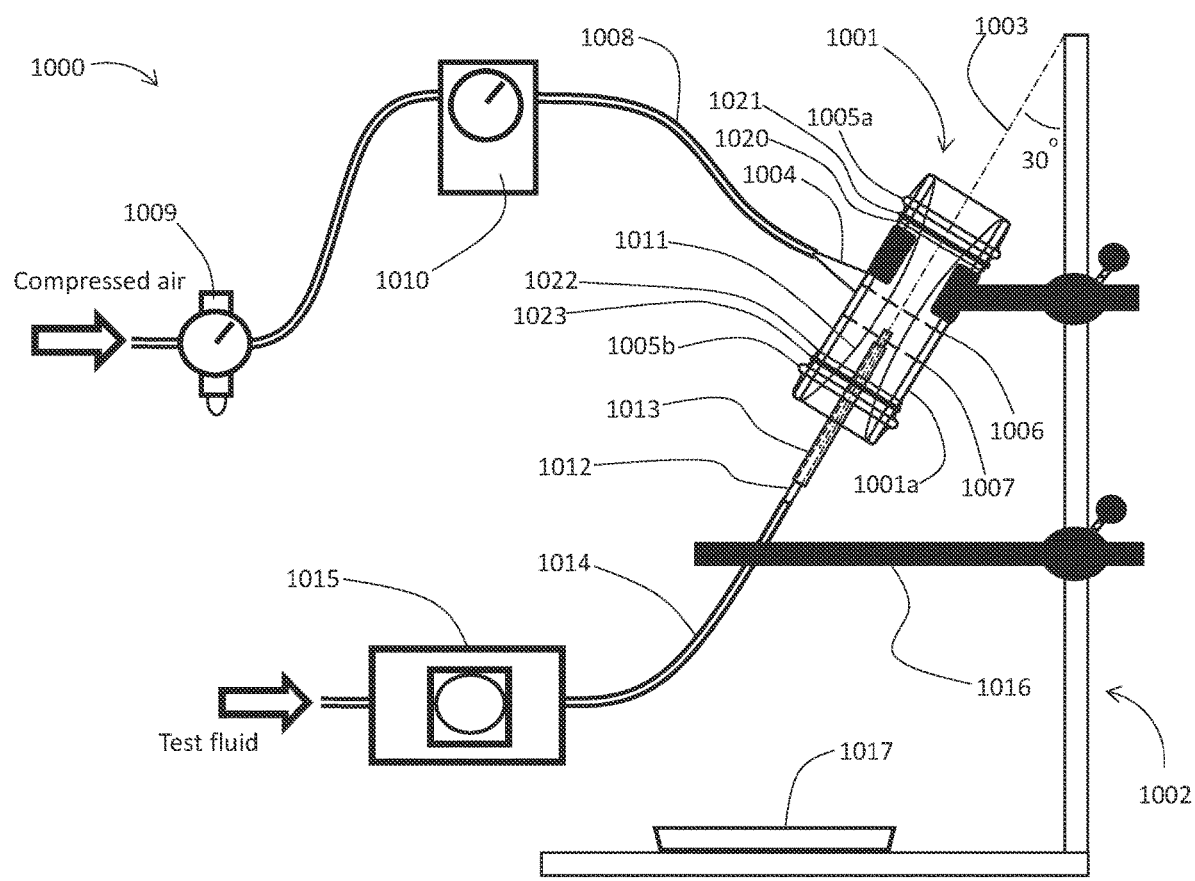
FIGS. 9A and 9B are schematic depictions of a configuration of equipment used in the Wicking Measurement method herein.

The measurement apparatus 1000 is schematically depicted in FIG. 9A. The measurement apparatus 1000 includes a wicking chamber 1001 including a hollow glass tube 1001a mounted to a ring stand 1002 in such a way that the longitudinal axis 1003 of the tube 1001a lies within a vertical plane and is 30 o+2 o from a vertical line. The glass tube 1001a is open at both ends, and has a 3.3 cm inner diameter, a 3.8 cm outer diameter, and an overall length of 10.5 cm. The glass tube 1001a has a'/4 inch hose barb 1004 (that provides fluid communication with the space inside the tube) located at its longitudinal midpoint, extending perpendicularly from the outer surface of the glass tube. Located about 7 mm from each end of the glass tube are circumferential sealing ridges 1005a, 1005b on the outside of the tube (which may be formed as "mamas," also known as "mariahs," as known in glassblowing art), each with a 48.0 mm outer diameter and oriented along a plane perpendicular to the longitudinal axis 1003 of the glass tube. Two lines 1006, 1007 are marked on the glass tube 1001a, both oriented along planes perpendicular to the longitudinal axis 1003 of the tube: the Pledget Base Line 1006 is marked at the longitudinal midpoint of the glass tube; the Cannula Position Line 1007 is marked 10.0 mm below the Pledget Base Line 1006. A compressed air source is connected to the hose barb 1004 with flexible tubing 1008. The air pressure is controlled via a pressure regulator 1009 and calibrated manometer 1010 (standardized to ANSI standards). The pressure regulator 1009 is set to 0.5+0.02 psi.

An unlubricated condom 1011 (complying with ASTM D3492) is installed inside the glass tube 1001a as follows. Unroll the condom 1011 and mark a Positioning Line thereon that is perpendicular to the longitudinal axis of the condom 1011 and located 12.0+0.1 cm from the open end.

Using a glass rod inserted into the condom 1011, push the condom 1011, closed/tip end first, into the lower open end of the glass tube 1001a, up through the tube and out the upper open end. Cut off the tip of the closed end of the condom 1011 (no more than about 1 cm from the tip) and discard the cutoff portion. Align the Positioning Line marked on the condom with the edge of the open upper end of the glass tube 1001a. Now, stretch and pull the newly cut edge 1020 of the condom 1011 radially out, down and over the circumference of the upper edge of the glass tube 1001a, and downwardly over and past the upper sealing ridge 1005a. Secure the circumferential cut edge of the condom 1011 to the outside of the glass tube 1001a below the upper sealing ridge 1005a, using a first rubber band 1021. Now, from the bottom, gently pull the condom slightly taut longitudinally, and stretch the circumferential edge 1022 of the original open end of the condom 1011 radially out, up and over the circumference of the lower edge of the glass tube 1001a and upwardly past the lower sealing ridge 1005b, and secure the circumferential edge of the original open end of the condom 1011 to the outside of the glass tube 1001a above the lower sealing ridge 1005b, using a second rubber band 1023.

(The references "up", "down", "upper", "lower", and similar terms used in this measurement method description are relative the position of the glass tube when mounted to and held by the ring stand as shown in FIG. 9A. However, the condom may be installed within the glass tube before it is mounted on the ring stand. Similarly, the Pledget Base Line and Cannula Position Line on the glass tube as described above may be marked on the tube before it is mounted on the ring stand.)

The test fluid used (for purposes of providing a fluid having a suitable degree of similarity to human menstrual fluid) is defibrinated sheep's blood, with a packed cell volume between 38%-42% (such as that available from Cleveland Scientific Ltd., Bath, OH, or equivalent) and a viscosity between 6.5-8.0 centistokes. Prior to use in this measurement method, the viscosity of the test fluid is measured using a low viscosity rotary viscometer (a suitable instrument is the Cannon LV-2020 Rotary Viscometer with UL adapter, Cannon Instrument Co., State College, PA, or equivalent). The appropriate size spindle for the viscosity range is selected, and the instrument is operated and calibrated as per the manufacturer's instructions. Measurements are taken at 23° C.±1 C.° and at 60 rpm. Results are recorded to the nearest 0.01 centistokes and must be in spec before use.

The test fluid is placed in a 250 mL reservoir with a cover and continuously and moderately stirred to avoid separation. The temperature of the test fluid is maintained at 23° C.±2 C.° during use. The test fluid is supplied from the reservoir to a 15-gauge steel laboratory cannula 1012 (about 10 cm long with a blunt tip at each end with an inner diameter of 1.33-1.41 mm and an outer diameter of 1.82-1.84 mm (such as that available from Cadence Science Inc., 2080 Plainfield Pike, Cranston, RI 02921, or equivalent) and cannula sleeve 1013 (transparent flexible silicone tubing with 3.2 mm inner diameter, 4.8 mm outer diameter, about 7 cm long (such as that available from Cole Parmer, Verner Hills, IL, or equivalent) with peristaltic pump tubing 1014 that has an inner diameter of 1.6 mm. The cannula 1012 is inserted through the prepared cannula sleeve 1013 such that there is about 6 mm of the upper/distal tip of the cannula 1012 extending beyond the upper/distal edge of cannula sleeve 1013. (The purpose of the cannula sleeve, of an inner diameter greater than the outer diameter of the cannula, is to provide a pathway for fluid that is not captured and wicked after contacting the wicking member, to flow under gravitational pull down and out of the test chamber, thereby helping reduce chances of pooling of the fluid within the test chamber.) The lower end of the cannula 1012 is inserted into the peristaltic pump tubing 1014. A peristaltic pump 1015 (such as Master Flex, available from Cole Parmer, Verner Hills, IL, or equivalent) is programmed to deliver 5.0 g+0.25 g of test fluid at 1.0 g/min±0.02 g/min (i.e., over a 5-minute period of operation of the pump). Prior to commencement of the measurement, the peristaltic pump 1015 is calibrated with the test fluid, and the tubing 1014 and cannula 1012 are then primed with test fluid.

A cannula stabilizing bar 1016 is mounted to the ring stand 1002 such that it is about 2 cm below the bottom of the wicking chamber 1001, however, this position can be adjusted as needed. The cannula stabilizing bar 1016 is used to support the peristaltic pump tubing 1014 in order to allow the cannula 1012 to be maintained in a position in which its longitudinal axis is approximately parallel to longitudinal axis 1003 of the glass tube 1001a during the measurement.

Tampon measurement samples still in their applicators and covers are conditioned at 23° C.±2 C.° and 50±2% relative humidity for at least 2 hours prior to use. Measurement samples are not removed from their covers or applicators until immediately prior to use, and must be used within 30 minutes following removal. Clean disposable exam grade, nitrile rubber, powder-free medical gloves must be worn while preparing the measurement samples and during the measurement procedure in order to prevent any contamination from contact with the analyst's hands. Each tampon measurement sample is prepared by first removing the tampon 10 from its applicator in the manner the product is designed to effect ejection of the tampon from the applicator. Cut the withdrawal cord 12 from the tampon 10 at the trailing edge 15c of the wicking member 15. After cutting away such portion of the withdrawal cord, record the Dry Mass of the tampon measurement sample to the nearest 0.01 g.

Figure 9B:
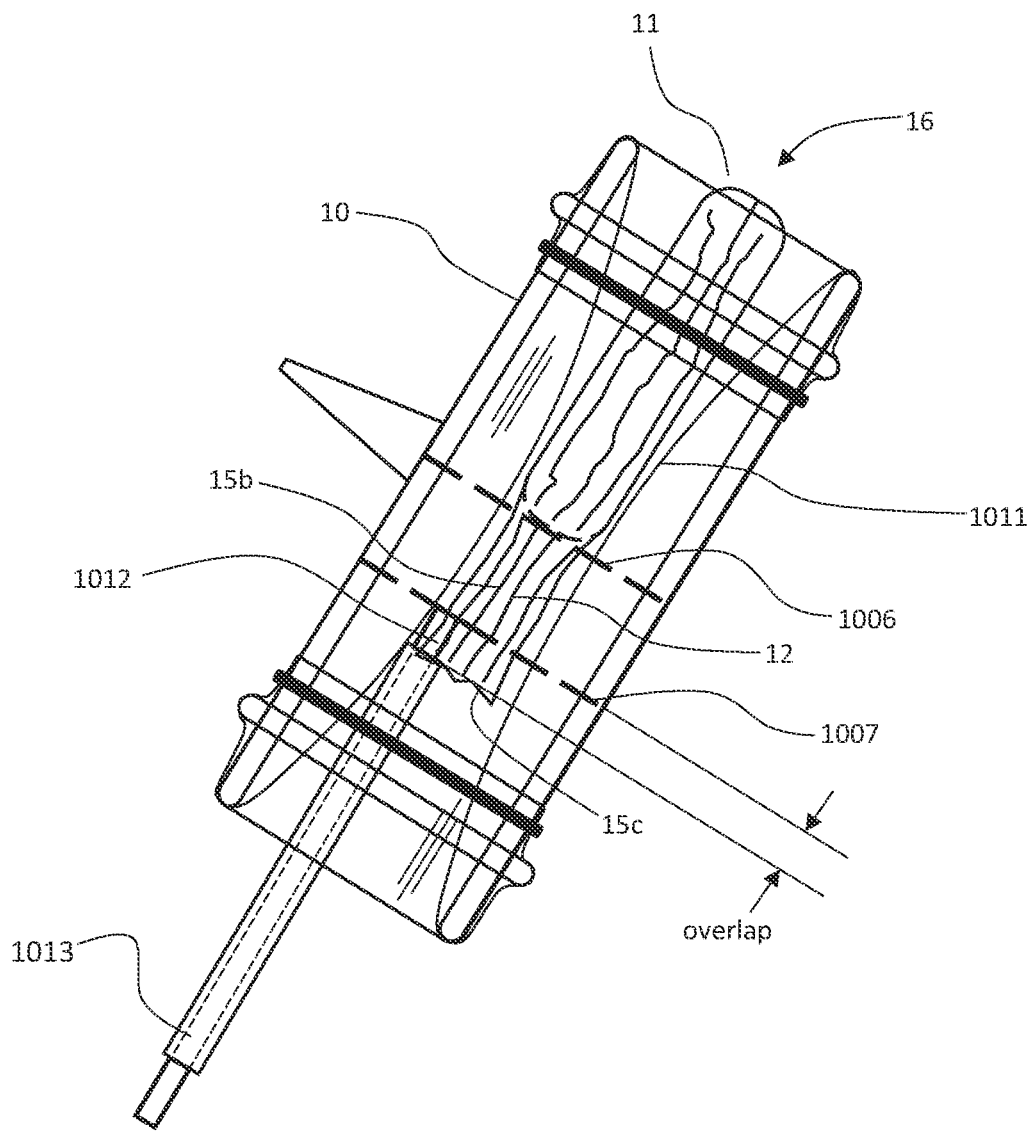

Now referring to FIG. 9B, the tampon measurement sample is placed into the unpressurized wicking chamber 1001 as follows. (An assistant may be required to assist in manipulating the measurement sample and cannula into position and holding them in position until the measurement chamber is pressurized.) Insert the forward end 16 of the pledget 11 into the bottom of the wicking chamber 1001 and move the sample upward in the chamber to a location at which the rearward end 17 of the pledget 11 is aligned with the Pledget Base Line 1006. Align the longitudinal axis of the pledget and wicking member 15 approximately with the longitudinal axis 1003 of the wicking chamber 1001. If the wicking member 15 and remaining portion of withdrawal cord 12 are not coaxial, rotate the tampon measurement sample about its longitudinal axis within the chamber, to a position in which the trailing portion 15b of the wicking member 15 occupies a predominantly dorsal (overlying) position relative the remaining portion of the withdrawal cord, and the remaining portion of the withdrawal cord 12 occupies a predominantly ventral (underlying) position relative the trailing portion 15b of the wicking member. While holding the measurement sample in place inside the wicking chamber 1001 in this position, insert the prepared cannula 1012 with attached cannula sleeve 1013 into the bottom of the wicking chamber 1001 and move it upward within the chamber to a position at which the upward tip of the cannula 1012 is aligned with the Cannula Position Line 1007, and positioned directly over and in contact with the dorsal surface of the wicking member 15, and longitudinally overlaps it by at least 5 mm. (If the trailing portion 15b of wicking member 15 of the particular tampon sample is shorter than 15 mm when in a straightened but substantially relaxed condition so as to provide≥5 mm overlap, position the cannula tip over the wicking member so that it overlaps the trailing end of the wicking member by ⅓ of the length of the trailing portion 15b. If the trailing portion 15b of wicking member 15 of the particular tampon sample is shorter than 6 mm when in a straightened but substantially relaxed condition, then the sample cannot be tested according to this method, and does not fall within the contemplation of claims herein that recite a value for Wicking.)

Now, pressurize the wicking chamber 1001 to 0.5+0.02 psi (over ambient air pressure) such that the condom 1011 inflates within the wicking chamber around the measurement sample and cannula 1012 to hold them in place inside the chamber 1001. Ensure that there is still a distance of 6 mm between the tip of the cannula 1012 and the edge of the cannula sleeve 1013. Adjust the position of the cannula stabilizing bar 1016 so that it supports the peristaltic pump tubing 1014 to allow the longitudinal axis of the cannula 1012 to be maintained in a position that is approximately parallel to the longitudinal axis 1003 of the wicking chamber 1001. Adjust as needed to maintain this position throughout the measurement.

Prior to starting of the peristaltic pump, a tray 1017 or other suitable collection means may be placed on the benchtop below the bottom of the cannula sleeve 1013 and wicking chamber 1001 to collect any test fluid that is not wicked/absorbed by the measurement sample and exits the bottom of the test chamber.

Start the peristaltic pump 1015 to deliver 5.0 g+0.25 g of test fluid at 1.0 g/min±0.02 g/min through the cannula 1012. While the test fluid is being delivered, ensure that the tip of the cannula 1012 remains in contact with the trailing portion 15b of the wicking member 15 and that there is no pooling of fluid in a crease in the condom 1011 proximate the cannula tip. If pooling of test fluid is observed, move the cannula 1012 slightly further down the trailing portion 15b of the wicking member 15. If pooling of test fluid continues, discard the tampon and repeat using a new measurement sample.

After the pump stops, depressurize the wicking chamber 1001 and remove the test sample. Record the Wet Mass of the test sample to the nearest 0.01 g. Calculate the mass of fluid absorbed by the test sample as Wet Mass—Dry Mass and record as Total Uptake to the nearest 0.01 g. The condom 1011 is wiped clean in between test samples and replaced after every 10 samples are tested.

In like fashion, repeat for a total of ten replicate test samples. Calculate the arithmetic mean for Total Uptake measured across all ten replicate test samples and report to the nearest 0.01 g.

In view of the foregoing description, the following non-limiting examples are contemplated:

1. A tampon (10) having a longitudinal axis (100) along a use insertion direction, the tampon comprising a pledget (11) having a forward end (16) and a rearward end (17); a wicking member (15) having a trailing portion (15b) trailing the rearward end (17) and having a rearward edge (15c); and a withdrawal cord (12) with an attached portion (12a) attached to the pledget, and a free portion (12b) trailing the rearward end (17) and the rearward edge (15c);
wherein:
when in an opened condition the pledget (11) has a pair of side edges (18), a first broad surface (35) and a second broad surface (36) opposite the first broad surface, the first and second broad surfaces occupying approximately parallel planes; the pledget (11) having a pledget length PL and a pledget width PW;
the pledget comprises a batt of one or more layers of fibrous absorbent material (32) and an outer cover (30) at least partially covering the absorbent material and comprising a first section of nonwoven web material,
the trailing portion (15b) of the wicking member (15) comprises at least four layers of nonwoven web material, at least one of the layers being formed of an integral extension of the first section of nonwoven web material;
the wicking member (15) has a wicking member width WW substantially equal to the pledget width PW; and
the trailing portion (15b) has a wicking member length WL of at least about 10 mm, more preferably at least about 15 mm, and even more preferably at least about 20 mm, and no greater than about 60 mm, more preferably no greater than about 50 mm, even more preferably no greater than about 40 mm, and still more preferably no greater than about 30 mm.

2. The tampon of example 1, wherein the outer cover (30) wraps over the absorbent material (32) at the forward end (16).

3. The tampon of either of the preceding examples, wherein the first section of nonwoven web material integrally forms the entirety of the outer cover (30) and at least two layers of the wicking member (15).

4. The tampon of example 3, wherein the first section of nonwoven web material integrally forms the entirety of the outer cover (30) and all four layers of the wicking member (15).

6. The tampon of any of the preceding examples, wherein the rearward edge (15c) of the wicking member (15) is formed by a fold in nonwoven web material.

7. The tampon of any of the preceding examples, wherein the outer cover (30) is held to the pledget (11) by stitches (40).

8. The tampon of any of the preceding examples, wherein all four layers of the wicking member are held to the pledget and/or to the withdrawal cord by stitches (40).

9. The tampon of any of the preceding examples, wherein the attached portion (12a) of the withdrawal cord (12) is attached to the pledget (11) via stitches (40) that penetrate the withdrawal cord and the pledget.

10. The tampon of example 9 wherein both the outer cover (30) and the attached portion (12a) of the withdrawal cord (12) are held to the pledget by the stitches (40).

11. The tampon of any of the preceding examples wherein the outer cover (30) is not bonded substantially to the absorbent material (32) via thermal bonding, pressure bonding or adhesive.

12. The tampon of any of the preceding examples wherein the first section of nonwoven web material is not bonded substantially to itself via thermal bonding, pressure bonding or adhesive.

13. The tampon of any of the preceding examples wherein the layers of the wicking member (15) are not bonded substantially to the absorbent material (32) or to themselves via thermal bonding, pressure bonding or adhesive.

14. The tampon of any of the preceding examples wherein the outer cover (30) has an overlapping portion (30a) wherein the first section of nonwoven web material overlaps itself.

15. The tampon of example 14 wherein the overlapping portion (30a) terminates at a rearwardmost extent thereof with an exposed overlapping edge (30b).

16. The tampon of any of the preceding examples wherein the tampon has been compressed primarily in a lateral direction from an open condition to a substantially cylindrical self-sustaining form.

17. The tampon of any of the preceding examples wherein the first section of nonwoven web material comprises a spunbond material comprising polypropylene fibers, treated to be rendered hydrophilic.

18. The tampon of example 17 wherein the spunbond material has a basis weight of 10 gsm to 30 gsm, more preferably 15 gsm to 25 gsm, and even more preferably 17 gsm to 22 gsm.

19. The tampon of any of examples 1-16 wherein the first section of nonwoven web material comprises fibers selected from the group consisting of cotton fibers, rayon fibers, spun thermoplastic polymer fibers and combinations thereof.

20. The tampon of example 19 wherein the first section of nonwoven web material comprises rayon fibers and spun thermoplastic polymer fibers in a weight ratio of from 33:67 to 67:33, more preferably from 40:60 to 60:40, and even more preferably from 46:54 to 54:46, weight of rayon fibers to weight of spun thermoplastic polymer fibers.

21. The tampon of example 20 wherein the spun thermoplastic polymer fibers comprise polymer selected from the group consisting of polypropylene, polyester, polyethylene terephthalate (PET), polyethylene, and combinations thereof.

22. The tampon of claim 21 wherein the spun thermoplastic polymer fibers comprise predominantly PET.

23. The tampon of any of examples 19-22 wherein the first section of nonwoven web material comprises carded fibers that have been consolidated and entangled in a z-direction, the first section of nonwoven web material preferably having a basis weight of 15 gsm to 55 gsm, more preferably 25 gsm to 45 gsm, and even more preferably 30 gsm to 40 gsm.

24. The tampon of any of the preceding examples wherein at least one of the four layers of the wicking member are formed of one or more additional sections of nonwoven web material discrete from the first section of nonwoven web material.

25. The tampon of example 24 wherein the one or more additional sections of nonwoven web material comprise(s) a spunbond material comprising polypropylene fibers, treated to be rendered hydrophilic.

26. The tampon of example 25 wherein the spunbond material has a basis weight of 10 gsm to 30 gsm, more preferably 15 gsm to 25 gsm, and even more preferably 17 gsm to 22 gsm.

27. The tampon of example 24 wherein the one or more additional sections of nonwoven web material comprise(s) fibers selected from the group consisting of cotton fibers, rayon fibers, thermoplastic polymer fibers and combinations thereof.

28. The tampon of example 27 wherein the one or more additional sections of nonwoven web material comprise(s) rayon fibers and spun thermoplastic polymer fibers in a weight ratio of from 33:67 to 67:33, more preferably from 40:60 to 60:40, and even more preferably from 46:54 to 54:46, weight of rayon fibers to weight of spun thermoplastic polymer fibers.

29. The tampon of example 28 wherein the spun thermoplastic polymer fibers comprise polymer selected from the group consisting of polypropylene, polyester, polyethylene terephthalate (PET), polyethylene, and combinations thereof.

30. The tampon of claim 29 wherein the spun thermoplastic polymer fibers comprise predominantly PET.

31. The tampon of any of examples 27-30 wherein the one or more additional sections of nonwoven web material comprise(s) carded fibers that have been consolidated and entangled in a z-direction, the first section of nonwoven web material preferably having a basis weight of 15 gsm to 55 gsm, more preferably 25 gsm to 45 gsm, and even more preferably 30 gsm to 40 gsm.

32. The tampon of any of the preceding examples wherein the fibrous absorbent material (32) comprises fibrous material selected from the group consisting of cotton fiber, rayon fiber and combinations thereof.

33. The tampon of example 32 wherein the fibrous absorbent material (32) comprises predominantly rayon fiber.

34. The tampon of example 33 wherein the fibrous absorbent material (32) comprises substantially entirely rayon fiber.

35. The tampon of any of the preceding examples wherein the withdrawal cord comprises twisted or knitted fibrous material that is hydrophobic, or has been treated to be hydrophobic.

36. The tampon of any of the preceding examples wherein at least three layers of material forming the wicking member overlap the absorbent material 32 by at least 2 percent, more preferably at least 3 percent, and even more preferably at least 4 percent, of the length PL of the pledget 11.

37. The tampon of any of the preceding examples that exhibits wicking of at least 1.2 grams, more preferably at least 1.5 grams and even more preferably at least 1.8 grams, up to 3.2 grams, more preferably up to 4 grams, and even more preferably up to 5 grams.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed:

1. A tampon having a longitudinal axis along a use insertion direction, the tampon comprising a pledget having a forward end and a rearward end; a wicking member having a trailing portion trailing the rearward end and having a rearward edge; and a withdrawal cord with an attached portion attached to the pledget, and a free portion trailing the rearward end and the rearward edge;
wherein:
when in an opened condition the pledget has a pair of side edges, a first broad surface and a second broad surface opposite the first broad surface, the first and second broad surfaces occupying approximately parallel planes; the pledget having a pledget length PL and a pledget width PW;
the pledget comprises a batt of one or more layers of fibrous absorbent material and an outer cover at least partially covering the absorbent material such that a portion of the outer cover extends over the forward end of the one or more layers of fibrous absorbent material and comprising a first section of nonwoven web material,
the trailing portion of the wicking member comprises at least four layers of nonwoven web material, at least one of the at least four layers of nonwoven web material being formed of an integral extension of the first section of nonwoven web material;
the wicking member has a wicking member width WW substantially equal to the pledget width PW; and
the trailing portion of the wicking member has a length WL of at least about 10 mm and no greater than about 60 mm.

2. The tampon of claim 1, wherein the first section of nonwoven web material integrally forms the entirety of the outer cover and at least two layers of the wicking member.

3. The tampon of claim 2, wherein the first section of nonwoven web material integrally forms the entirety of the outer cover and all four layers of the wicking member.

4. The tampon of claim 1, wherein the rearward edge of the wicking member is formed by a fold in nonwoven web material.

5. The tampon of claim 1, wherein the outer cover is held to the pledget by stitches.

6. The tampon of claim 1, wherein all four layers of the wicking member are held to the pledget and/or to the withdrawal cord by stitches.

7. The tampon of claim 1, wherein the attached portion of the withdrawal cord is attached to the pledget via stitches that penetrate the withdrawal cord and the pledget.

8. The tampon of claim 7, wherein both the outer cover and the attached portion of the withdrawal cord are held to the pledget by the stitches.

9. The tampon of claim 1, wherein the tampon has been compressed primarily in a lateral direction from an open condition to a substantially cylindrical self-sustaining form.

10. The tampon of claim 1, wherein the first section of nonwoven web material comprises fibers selected from the group consisting of cotton fibers, rayon fibers, spun thermoplastic polymer fibers and combinations thereof.

11. The tampon of claim 10, wherein the first section of nonwoven web material comprises rayon fibers and spun thermoplastic polymer fibers, wherein a weight ratio of rayon fibers to spun thermoplastic polymer fibers is from 33:67 to 67:33.

12. The tampon of claim 11, wherein the spun thermoplastic polymer fibers comprise polymer selected from the group consisting of polypropylene, polyester, polyethylene terephthalate (PET), polyethylene, and combinations thereof.

13. The tampon of claim 12, wherein the spun thermoplastic polymer fibers comprise predominantly PET.

14. The tampon of claim 10, wherein the first section of nonwoven web material comprises carded fibers that have been consolidated and entangled in a z-direction, the first section of nonwoven web material having a basis weight of 15 gsm to 55 gsm.

15. The tampon of claim 1, wherein the fibrous absorbent material comprises fibrous material selected from the group consisting of cotton fiber, rayon fiber and combinations thereof.

16. The tampon of claim 15, wherein the fibrous absorbent material comprises predominantly rayon fiber.

17. The tampon of claim 1, wherein the withdrawal cord comprises twisted or knitted fibrous material that is hydrophobic, or has been treated to be hydrophobic.

18. The tampon of claim 1, wherein at least three layers of material forming the wicking member overlap the absorbent material 32 by at least 2 percent.

19. The tampon of claim 1, that exhibits wicking of at least 1.2 grams.

* * * * *